United States Patent [19]
Bauman et al.

[11] Patent Number: 5,830,767
[45] Date of Patent: Nov. 3, 1998

[54] CERAMIC ASSEMBLY FOR USE IN BIOLOGICAL ASSAYS

[75] Inventors: David S. Bauman, Norman, Okla.; Chad A. Sheckler, Phelps, N.Y.; Randy J. Grellner, Tulsa; Greg A. Griffeth, Cushing, both of Okla.

[73] Assignee: At Point Bio, Norman, Okla.

[21] Appl. No.: 713,160

[22] Filed: Sep. 12, 1996

Related U.S. Application Data

[60] Provisional application No. 60/007,509, Nov. 22, 1995.

Related U.S. Application Data

[63] Continuation-in-part of Ser. No. 583,874, Jan. 11, 1996, and Ser. No. 370,674, Jan. 10, 1995.

[51] Int. Cl.⁶ ........................ G01N 33/551; G01N 33/552

[52] U.S. Cl. .............................. 436/527; 422/55; 422/57; 422/58; 435/6; 435/287.1; 435/587.2; 435/287.7; 435/810; 436/518; 436/524; 436/810

[58] Field of Search .................................. 422/55, 56, 57, 422/58; 435/6, 287.1, 287.2, 287.7, 810; 436/518, 524, 527, 810

*Primary Examiner*—Christopher L. Chin
*Attorney, Agent, or Firm*—Howard J. Greenwald

[57] ABSTRACT

An assembly for use in biological assays containing an integral ceramic core and, partially abutting the core, a sheath. The ceramic core has a mean pore size of from about 1 to about 400 microns, an apparent porosity of from, about 25 to about 60 percent, a hydrophilic surface, a length of from about 10 to about 200 millimeters, and a wicking rate of at least about 20 millimeters per minute; the sheath has a wicking rate of less than 5 millimeters per minute.

10 Claims, 12 Drawing Sheets

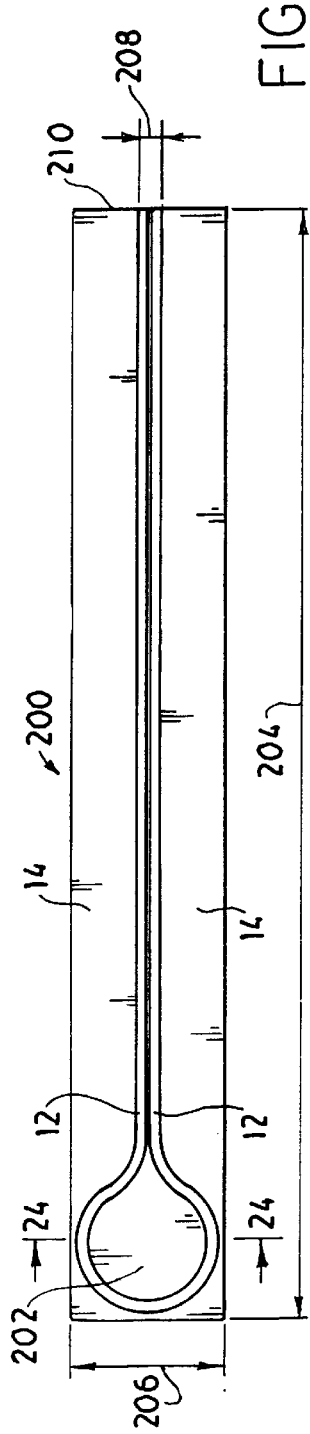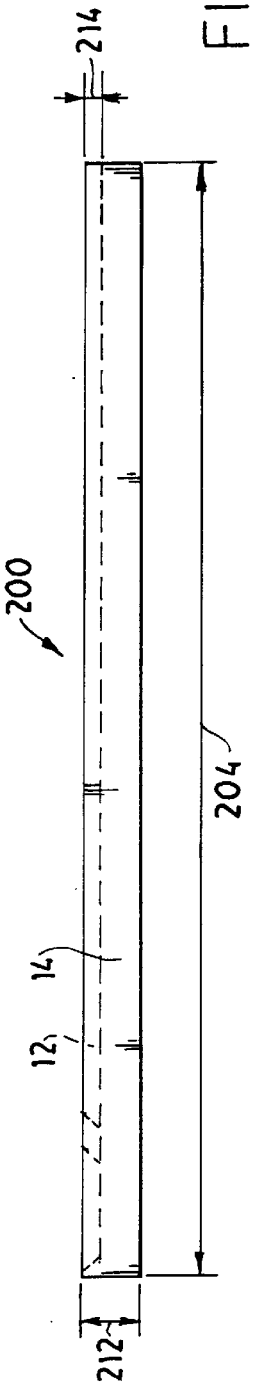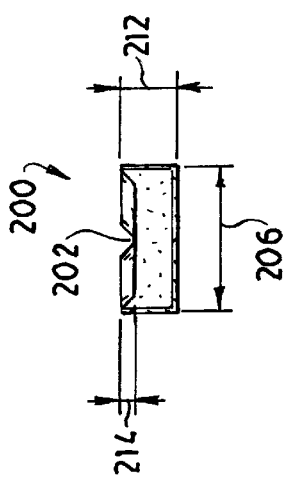

CERAMIC ASSEMBLY FOR USE IN BIOLOGICAL ASSAYS

REFERENCE TO RELATED PATENT APPLICATION

This application is a continuation-in-part of applicants' copending patent applications U.S. Ser. No. 08/583,874 (filed Jan. 11, 1996), U.S. Ser. No. 08/370,674, (filed Jan. 10, 1995), and U.S. Ser. No. 60/007,509 (filed Nov. 22, 1995).

FIELD OF THE INVENTION

A solid structure, for use in biological assays, which is formed of a porous ceramic core.

BACKGROUND OF THE INVENTION

Bioassays come in many forms and utilize a wide variety of reactants, including proteins (such as antibodies or antigens) and nucleic acids. These assays often utilize complementary oligonucleotides which selectively hybridize to the substance to be detected. Some typical assays are discussed below by reference to certain patents, the disclosures of which are hereby incorporated by reference into this specification.

U.S. Pat. No. 3,654,090 of Schuurs et al. discloses a process in which an antigen is attached to an enzyme, and an antibody is insolubilized by attachment to an insoluble carrier. In the process of this patent, the enzyme-labeled antigen and the insolubilized antibody are mixed with an unlabeled antigen (the assay substance). By controlling the amount of insolubilized antibody and enzyme-labeled antigen, some or all of the enzyme-labeled antigen is not attached to antibody when unlabeled antigen is present. Some or none of the enzyme-labeled antigen is attached. After mixing, the insoluble material is separated by centrifugation or washing from the soluble material, which includes any unattached enzyme-labeled antigen. An enzyme-reactive agent is then added to either the insoluble or soluble portions to assay the enzyme activity and to determine the presence of unlabeled antigen.

U.S. Pat. No. 3,966,897 of Renn et al. discloses an assay similar to that described in the Schuurs et al. patent in which the component is radioactively labeled instead of enzyme labeled. This patent discloses that indicator dyes can be attached to the components and then directly measured by visual examination, fluorimetry, spectrophotometry, or refractometry.

European patent DP 0 291 194 B1 (assigned to Unilever N. V.) discloses a device which is useful for sandwich assays involving multiple zones for detection of analyte in a sample. In one embodiment of this patent, sample is added to a first zone formed of a porous material (such as porous plastic or nitrocellulose) which contains antibody to a first epitope of the analyte, where the antibody is labeled with a readily detectable label (such as a colored latex particle having a diameter of from about 0.05 to about 0.5 microns). A second zone in the porous material contains immobilized antibody to a second epitope of the analyte. A positive result is obtained when the labeled antibody and the immobilized antibody are coupled to each other via the analyte.

The deficiencies of the prior art assay structures correspond to substantial disadvantages in the use of these structures. Thus, for example, the prior art assays used for determining whether domestic animals are pregnant are relatively complicated, expensive, and inaccurate.

Thus, for example, U.S. Pat. No. 4,744,368 discloses a method for detecting pregnancy in farm animals in which an electrically conductive finger receptacle is placed on the end of a person's finger, an electrical transducer is placed within the uterus of the farm animal, in contact with the uterine artery, and the person's finger with its attached finger receptacle is then stuck up the animal's uterus until contact is made with the conductive portion of the electrical transducer. This method clearly requires the restraint of and/or the cooperation of the animal, it can only be used with animals with sufficiently large uteri, and even with such animals it requires accurate placement of the conductive finger on the conductive portion of the transducer. After the test has been conducted, the transducer must be removed from the animal. Furthermore, since one is attempting to measure blood flow through the artery, the fact that the test method affects blood flow through the artery makes the results obtained somewhat suspect.

It is an object of this invention to provide a novel assay assembly which can be economically made in various shapes and sizes for use in diagnostic assays.

It is another object of this invention to provide an assay assembly for diagnostic and industrial use which can be decontaminated and disposed of without any substantially adverse environmental impact.

It is another object of this invention to provide a novel assembly which can be used in diagnostic assay structures and which provides consistent, accurate, linear displacement readings.

It is yet another object of this invention to provide a assay for determining when an animal is pregnant which is accurate, inexpensive, and easy to perform.

SUMMARY OF THE INVENTION

In accordance with this invention, there is provided an assay for determining whether a farm animal is pregnant. This assay utilizes an assembly which contains an integral ceramic core which has a mean pore size of from 1 to 400 microns, an apparent porosity of from about 25 to about 60 percent, and a wicking rate of at least about 20 millimeters per minute. Substantially homogeneously disposed throughout the ceramic core is from about 0.01 to about 1 weight percent of biologically active molecules.

BRIEF DESCRIPTION OF THE DRAWINGS

The present invention will be more fully understood by reference to the following detailed description thereof, when read in conjunction with the attached drawings, wherein like reference numerals refer to like elements, and wherein:

FIG. 22 is a top view of another preferred assembly of this invention;

FIG. 23 is a side view of the assembly of FIG. 22;

FIG. 24 is an end view of the assembly of FIG. 23; and

DESCRIPTION OF THE PREFERRED EMBODIMENTS

In the first part of this application, a preferred assembly for use in the assay of the invention will be described. Thereafter, the preferred assay of the invention will be described.

Figure 1:
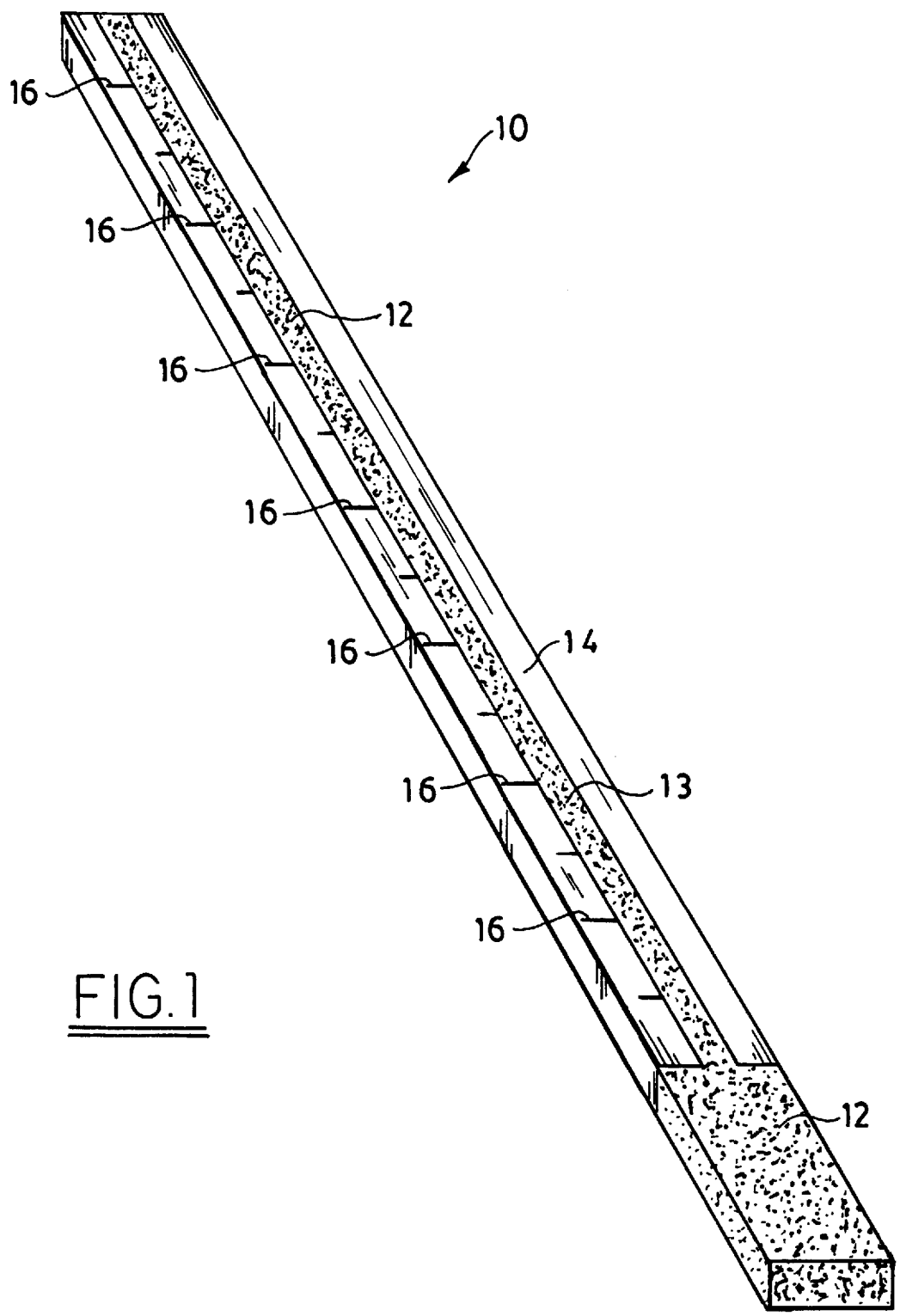
FIG. 1 is a perspective view of one preferred assay assembly of the invention.

FIG. 1 is a perspective view of one solid assay assembly 10 of the invention which is comprised of a core material 12 with a hydrophilic surface 13 which has a strong affinity for water; see, e.g., A.S.T.M. Standard Tests B374-80/1985 ("Definitions of Terms Relating to Electroplating"), C813-75/1985 ("Test Method for Hydrophobic Contamination on Glass by Contact Angle Measurement"), and D1695-75/1983 ("Definition of Terms Relating to Cellulose and Cellulose Derivatives").

Without wishing to be bound to any particular theory, applicants believe that a hydrophobic surface is undesirable since most bioassays are performed in aqueous medium and hydrophobic adsorption can result in an uncontrolled assay baseline.

Support materials with hydrophilic surfaces are well known to those skilled in the art. Thus, e.g., reference may be had to U.S. Pat. No. 5,425,998 (a hydrophilic surface comprised of colloidal silica particles 20 nanometers or less in diameter, a slip agent, and an adhesive), U.S. Pat. Nos. 5,409,799, 5,401,611, 5,401,482 (talc substances with hydrophilic surfaces properties), U.S. Pat. Nos. 5,395,730, 5,369,012, 5,352,711 (hydrophilic absorbent foam material), U.S. Pat. No. 5,324,548, 5,306,632, 5,264,917, 5,254,143, 5,229,094 (talc substances with hydrophilic surfaces), U.S. Pat. Nos. 5,219,687, 5,206,298, 5,200,037 (surface hydrophilic latexes), U.S. Pat. Nos. 5,196,227, 5,175,050 (polyester with hydrophilic surfaces), U.S. Pat. No. 5,158,728 (porous membrane with hydrophilic surface), and the like. The disclosure of each of these United States patents is hereby incorporated by reference into this specification.

Figure 2:
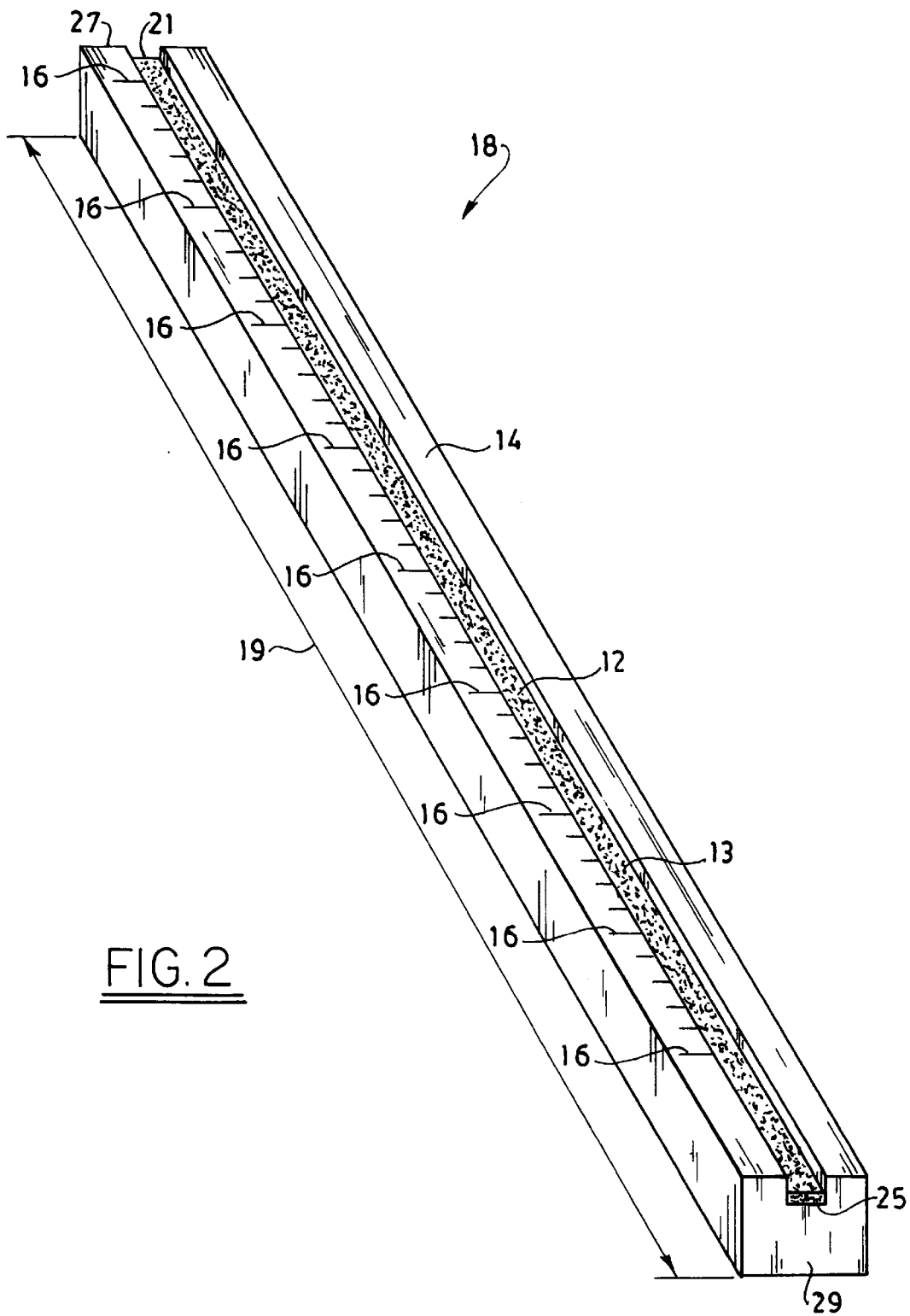
FIG. 2 is a perspective view of another preferred as say assembly of the invention.

In one preferred embodiment, depicted in FIGS. 1 and 2, the core material 12 is an integral structure which comprises a ceramic structure 12 integrally connected to and partially encapsulated within a sheath structure 14. Means for preparing ceramic composite materials are known to those in the art. Thus, reference may be had to U.S. Pat. No. 4,629,483 (formation of a fine pored outer layer of alumina on a coarse, permeable inner layer of alumina), U.S. Pat. No. 5,215,686 (formation of a rigid, monolithic diffusion element comprised of a porous alumina core coated with a fine pored alumina coating), and the like. The disclosure of each of these United States patents is hereby incorporated by reference into this specification.

Support assembly 10 is preferably comprised of ceramic core 12 preferably disposed within sheath 14. Marks 16 indicate how far up the column of core material 12 a material to be tested (an "analyte") migrates.

In one embodiment, the surface 13 of ceramic core 12 has a refractive index which is substantially identical to the refractive index of the solvent used to carry the analyte/indicator particles or molecules used in the process of this invention. Either the raw ceramic material and/or the solvent used can be chosen to have such compatible optical properties, and/or either or both of these components may have their optical properties modified by the addition of modifying agents. Thus, in one embodiment, sucrose, dextran, carrier proteins (such as bovine serum albumen), sodium silicate, and/or other agents may be added to the solvent to raise the refractive index of the solution so that is within about 10 percent of the refractive index of the ceramic. When the solvent/analyte/indicator complex travels up ceramic core 12, the solvent will make the ceramic core substantially transparent because of the substantial match in the refractive indices. However, the binding of the analyte and indicator complex in the reading zones of the device will destroy this transparency, thereby making the demarcation line visually apparent. When the analyte/indicator complex has been exhausted, only solvent will continue to migrate by capillary migration, and will create a contiguous transparent zone.

In one embodiment, the analyte/indicator complex used will be colored (such as colored latex, colloidal gold sol, colored ceramic particles).

In one preferred embodiment, illustrated in FIG. 1, the surface 13 of core 12 is substantially opaque. In another embodiment, not shown, the surface 13 has a white color.

Another composite assay assembly 18 which may be used is illustrated in FIG. 2. Referring to FIG. 2, it will be seen that support assembly 18 is preferably comprised of a ceramic core 12 preferably disposed within sheath 14. Marks 16 to which suitable indicia (not shown) are affixed are disposed on the surface of material 14 and indicate how far up the column of material 12 a material to be tested migrates.

In the preferred embodiment depicted in FIG. 2, ceramic core 12 (and support 18) has a length 19 which is from about 10 to about 200 millimeters and, more preferably, is from about 20 to about 100 millimeters. In a more preferred embodiment, length 19 is from about 40 to about 80 millimeters.

Ceramic core 12 has a top surface 21 and a bottom surface 25. Similarly, sheath 14 also has a top surface 27, and a bottom surface 29.

The wicking rate of ceramic core 12 may be determined by a test in which a strip of ceramic core 12 is placed with its bottom surface 25 disposed in a layer of distilled water (not shown) which is at a temperature of 25 degrees Centigrade and has a depth of 3.5 millimeters. The extent to which the distilled water wicks up the core 12 for in a period of 10 minutes is determined, and the wicking rate (the number of millimeters traveled per minute) is then calculated.

The wicking rate of sheath 14 may be determined by a similar test in which the bottom surface 29 of the sheath 14 is also placed is distilled water at a temperature of 25 degrees Centigrade.

The wicking rate of the ceramic core 12 is preferably at least about 20 millimeters per minute. In more preferred embodiment, the wicking rate of the ceramic core 12 is at least about 50 millimeters per minute. By comparison, the wicking rate of the sheath 14 is less than about 5 millimeters per minute; sheath 14 is substantially non-wicking. The ratio of the wicking rate of the ceramic core 12 to the sheath 14 is at least about 4/1 and, more preferably, at least about 10/1.

Figure 3:
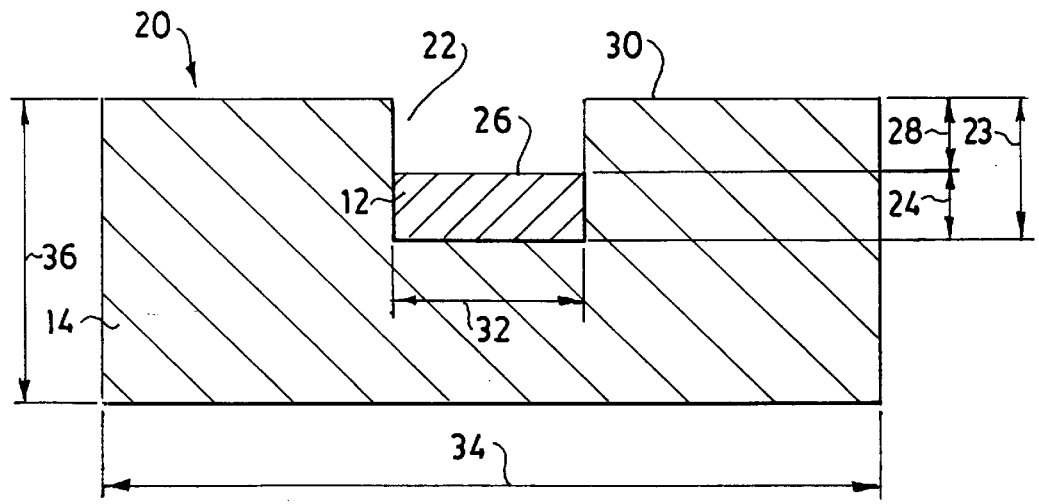
FIG. 3 is an enlarged sectional view of the assembly of FIG. 2.

FIG. 3 is an enlarged sectional view of the support 20 of FIG. 2. Referring to FIG. 3, it will be seen that ceramic core 12 is preferably disposed within a channel 22 formed within sheath 14. Channel 22 preferably has a depth 23 of from about 1 to about 5 millimeters and, more preferably, from about 1 to about 2 millimeters.

In the preferred embodiment depicted in FIGS. 2 and 3, the ceramic core 12 has a thickness 24 of from about 0.1 to about 2 millimeters, and, preferably, has a thickness 24 of 1 from about 0.1 to about 1 millimeters. The top wall 26 of ceramic core 12 is preferably disposed a distance 28 from the top wall 30 of sheath 14 of from about 0.1 to about 3 millimeters. The ceramic core 12 preferably has a width 32 of from about 0.5 to about 11 millimeters and, more preferably, from about 0.5 to about 2 millimeters.

In one embodiment, the ceramic core 12 has a thickness 24 which is at least about 10 times the mean pore diameter of ceramic core 12.

Referring again to FIG. 3, and in the preferred embodiment depicted therein, it will be seen that sheath 14 preferably has a substantially rectangular shape, with a width 4 of from about 6 to about 10 millimeters, and a height 36 of from about 2 to about 8 millimeters. In general, the ratio of width 34 to height 36 is preferably at least about 3/1.

Referring again to FIG. 3, it will also be seen that ceramic core 12 has a substantially rectangular cross-sectional shape. In other embodiments, not shown, ceramic core 12 may have a substantially circular, oval, irregular, or other cross-sectional shape.

Figure 4:
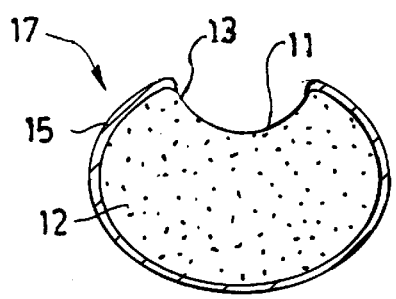
FIG. 4 is an end view of another assay assembly of the invention.

FIG. 4 is a sectional view of one preferred assembly 17 which has a substantially deflated ovoid shape. and which is comprised of porous ceramic material 12 which is partially coated with glaze 15. The unglazed portion 13 of assembly 17 presents a porous surface 11 which selectively encourages migration of the test solution up portion 13.

Figure 5:
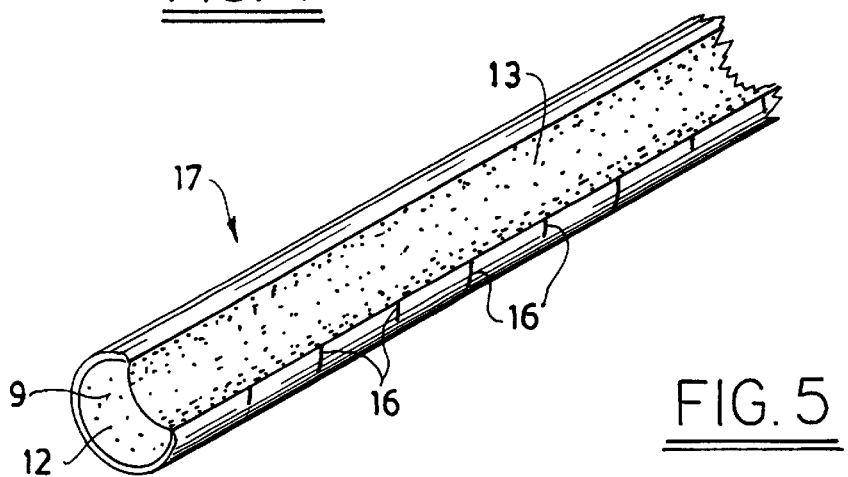
FIG. 5 is a perspective view of the assay assembly of FIG. 4.

FIG. 5 is a perspective view of the assembly 17 showing indicator marks 16 on the glazed upper surface of apparatus 17.

The assembly of FIGS. 4 and 5 can be made by a process in which a green body in the shape of a deflated ovoid (or other desired shape) is formed by standard forming techniques such as, e.g., extrusion or pressing. The green body is then preferably fired and, thereafter, glaze is applied to cover every portion of it except reading portion 13 and the unglazed end regions (such as, e.g., region 9 of FIG. 5). The partially glaze-covered assembly is then fired again.

Any conventional glaze application method can be used to apply glaze to selected portions of the green body. Thus, e.g., the glaze may be applied by a wet process, such as by spraying, waterfall, fountain, dipping, slinger, splatter, flash/mist, etc.; see, e.g., pages 573–581 of James S. Reed's "Principles of Ceramic Processing", Second Edition (John Wiley & Sons, New York, 1995). In one embodiment, the green body is rolled in glaze to contact glaze with every portion of it except the reading portion 13 and the unglazed end regions. Referring again to FIGS. 1–4, regardless of the cross-sectional shape of ceramic core 12, it is preferred that such ceramic core 12 have a cross-sectional perimeter of from about 2 to about 32 millimeters. It is preferred that from about 20 to about 90 percent of the perimeter of ceramic core 12 be contiguous with, supported by, and integrally connected to sheath 14. In one embodiment, from about 70 to about 90 percent of the perimeter of core 12 is contiguous with sheath 14.

In the embodiment depicted in FIGS. 2 and 3, there is no adhesive disposed between the walls of ceramic core 12 and sheath 14. In another embodiment, not shown, adhesive is disposed between the core 12 and the sheath 14; and the core 12 is bonded to and contiguous with the sheath 14. As used in this specification, the term bonded refers to a physical and/or a chemical bond formed between the core 12 and the sheath 14.

In both embodiments, at least some of the walls of ceramic core 12 are contiguous with and integrally connected to the sheath 14. This integral connection precludes the possibility of uncontrolled capillary migration in a void space (not shown) between the core 12 and the sheath 14. One may determine whether an integral connection exists between the core 12 and the sheath 14 by conventional means. Thus, by way of illustration and not limitation, and referring to FIG. 2, one may dip assembly 18 into a solution of colored particles which are too large to diffuse into the pores of either core 12 or sheath 14 but may enter any voids between such core 12 and sheath 14. The presence of any indicator test solution in any undesired gaps may then be visually determined.

Referring again to FIG. 1, it is preferred that ceramic core 12 be comprised of a multiplicity of pores and have a mean pore size of from about 1 to about 400 microns and, more preferably, from about 5 to about 100 microns. In one preferred embodiment, the mean pore size is from about 5 to about 20 microns.

The mean pore size is the average pore size of the body as determined by capillary attraction of the pores for a liquid of known surface tension. It may be determined in accordance with A.S.T.M. Standard Test F316-86, "Test Method for Pore Size Characteristics of Membrane Filters for Use with Aerospace Filters". Reference also may be had to U.S. Pat. No. 3,438,245 (device for measurement of pore size and pore volume), U.S. Pat. No. 3,683,674 (measurement of pore size and porosity), U.S. Pat. No. 4,170,129 (method for determining the pore volume distribution of a sample by mercury intrusion), U.S. Pat. No. 4,660,412 (three fluid method for non-mercury intrusion porosimetry), U.S. Pat. No. 4,926,113 (means and method for conductometric phase transition porosimetry), U.S. Pat. Nos. 5,385,801, 5,188,930 (mean pore size of a zeolite material), U.S. Pat. Nos. 5,281,437, 5,254,399, 5,240,472 (mean pore size of an alumina membrane), U.S. Pat. No. 5,221,484 (mean pore size of a microporous membrane), U.S. Pat. No. 5,207,915, 5,147,539, and the like, the disclosures of which are hereby incorporated by reference into this specification. Reference also may be had to John P. Sibilia's "A Guide to Materials Characterization and Chemical Analysis" (VCH Publishers, Inc., New York, N.Y.).

In one preferred embodiment, the mean pore size of ceramic core 12 is from about 2 to about 20 microns.

Referring again to FIG. 1, what is of most interest in most applications is the mean pore size of the surface 13 of core 12; for the visually detectable event which the assay preferably utilizes is apparent on surface 13. Thus, in one embodiment, not shown, core 12 is a composite structure with a surface 13 with one mean pore size, and a base (not shown) with another mean pore size.

The ceramic core 12 preferably has an apparent porosity of from about 25 to about 60 percent and, more preferably, from about 35 to about 55 percent. Apparent porosity is the relationship of the open pore space to the bulk volume, expressed in percent (see A.S.T.M. C242-87). It may be measured by conventional means such as, e.g., the mercury porosimetry means discussed above. Reference also may be had to U.S. Pat. Nos. 5,215,686 and 5,204,298, the disclosures of which are hereby incorporated by reference into this specification.

In one preferred embodiment, the ceramic core 12 has a specific surface area of from about 0.1 to about 20 square meters per gram and, more preferably, from about 0.5 to about 3 square meters per gram. Specific surface area is the ratio between the total surface area of a porous substrate and its total weight. See, e.g., U.S. Pat. No. 5,217,930 (surface area of a porous metal carbide), U.S. Pat. No. 5,240,692 (surface area of magnesium carbonate), U.S. Pat. No. 5,318,833 (surface area of porous silica), U.S. Pat. No. 5,397,758 (surface area of porous alumina), U.S. Pat. No. 5,397,752 (surface area of porous sepiolite), U.S. Pat. Nos. 5,409,531, 5,418,043, 5,427,761, 5,432,137, 5,440,029, and the like, the disclosure of each of which is hereby incorporated by reference into this specification.

The ceramic core 12 is preferably comprised of at least 80 weight percent of ceramic material and, more preferably, at least 85 weight percent of ceramic material. In an even more preferred embodiment, ceramic core 12 consists essentially of ceramic material. The core 12 may contain one, two, or several ceramic materials.

In one preferred embodiment, ceramic core 12 is comprised of a least 80 weight percent of ceramic material and at least about 5 weight percent of a binder, such as polyphenylene sulfide, polyphenylene oxide, nylon 66, and the like. In this embodiment, the ceramic green body is preferably pressed into the shape of ceramic core 12 which, thereafter, is integrally connected to sheath 14.

One may prepare a nylon-containing core 12 by the process disclosed in U.S. Pat. No. 5,114,584. One may prepare a polyphenylene oxide-containing core 12 by the process disclosed in U.S. Pat. No. 5,384,047. The disclosure of each of these United States patents is hereby incorporated by reference into this specification.

Other thermoplastic materials may be used such as, e.g., ketone-based resins such as, e.g., polyetherether ketone, polyether ketone, polyether sulfone, and the like; see, e.g., column 5 of U.S. Pat. No. 5,384,047.

The term ceramic material includes solid material produced from essentially inorganic, metallic and non-metallic substances. The ceramic material is preferably formed simultaneously or subsequently matured by the action of heat. See, e.g. A.S.T.M. C-242-87, "Definitions of Terms Relating to Ceramic Whitewares and Related Products." Thus, the ceramics include any of a class of inorganic, products such as metallic oxides, silicates, borides, carbides, or nitrides and mixtures or compounds of such materials.

In one embodiment, the ceramic material is a porous alumina substrate permeated with silica.

In one embodiment, the ceramic material in core 12 contains from about 0.01 to 1 weight percent (by total weight of ceramic material) of a functional group selected from the group consisting of amine groups, hydroxyl groups, carboxyl groups, sulfhydryl groups, phosphate groups, aldehyde groups, ketone groups, and mixtures thereof. In this embodiment, it is preferred that the functional group be selected from hydroxyl groups, amine groups, and sulfhydryl (SH) groups The ceramic material used may be a ceramic whiteware, i.e., a ceramic body which fires to a white or ivory color.

The ceramic material used may be glass, i.e., an inorganic product of fusion which has cooled to a rigid configuration without crystallizing. See, for example, George W. McLellan et al.'s "Glass Engineering Handbook," Third Edition (McGraw-Hill Book Company, New York, 1984). By way of illustration, some suitable glasses include sodium silicate glass, borosilicate glass, aluminosilicate glass, and the like.

The ceramic material is preferably porous. Methods for making ceramic articles with specified porosity characteristics are well known and are disclosed, e.g., in U.S. Pat. No. 4,230,773 (decreasing the porosity and surface roughness of ceramic substrates), U.S. Pat. No. 4,447,548 (high porosity ceramic materials and method for making the same), U.S. Pat. No. 4,629,483 (ceramic filter with plural layers of different porosity), U.S. Pat. No. 5,017,522 (ceramic bodies of controlled porosity and process for making the same), U.S. Pat. No. 5,143,636 (controlled porosity piezoelectric ceramic), U.S. Pat. No. 5,152,791 (artificial bone having ceramic layers of different porosity), U.S. Pat. No. 5,165,981 (ceramic substrate comprising a base with a porosity of less than 5 percent), U.S. Pat. No. 5,180,697 (process for preparing self-supporting, porous bodies by reactive infiltration of a metal into a boron carbide material), U.S. Pat. No. 5,183,609 (preparation of honeycomb ceramic structure in which variation of oxygen content controls pore formation), U.S. Pat. No. 5,183,785 (process for preparing an aluminum borate ceramic by decomposing boric acid-stabilized aluminum acetate to form an aluminum borate powder and is entering the powder to form an ceramic body), U.S. Pat. No. 5,187,128 (process for preparing a self-supporting boron nitride body by infiltration of a parent metal into a boron nitride material), U.S. Pat. No. 5,188,678 (preparing a combustion synthesis mixture, forming this mixture into a green body in a die, and carrying out the combustion synthesis in the die), U.S. Pat. No. 5,196,235 (process for the preparation of a ceramic composite material), U.S. Pat. No. 5,200,373 (high strength composite ceramic structure), U.S. Pat. No. 5,204,299 (a ceramic composite structure comprising a polycrystalline oxidation reaction product formed on oxidation of a body of molten parent metal with an oxidant), U.S. Pat. Nos. 5,206,198, 5,215,666 (a ceramic composite body with interconnected porosity having openings having a mean diameter of less than about 6 microns), U.S. Pat. Nos. 5,215,686, 5,215,943 (preparation of ceramic membranes with enhanced thermal stability), U.S. Pat. No. 5,219,802 (porous ceramic radiation plate), U.S. Pat. No. 5,227,342 (process for making porous ceramic materials whose porosity can be controlled by manipulating the sol used to make the material), U.S. Pat. No. 5,238,883 (preparation of self-supporting bodies by reactive infiltration of a parent metal into a boron donor material and a carbon donor material), U.S. Pat. No. 5,252,255 (use of organic powders to produce pores in a ceramic filter assembly), U.S. Pat. No. 5,256,347 (production of ceramic honeycomb structure with pore forming agents), U.S. Pat. No. 5,279,737 (process for producing a porous ceramic composite structure using combustion synthesis), U.S. Pat. No. 5,308,422 (process of making ceramic/metal composites with layers of different porosities), U.S. Pat. No. 5,279,904 (a refractory ceramic material with a porous base refractory material and a zirconia protective layer), U.S. Pat. No. 5,296,417 (self-supporting ceramic body with varying porosities), U.S. Pat. No. 5,296,419 (self-supporting ceramic bodies), U.S. Pat. No. 5,326,512 (use of polystyrene microspheres to form pores in a ceramic), U.S. Pat. Nos. 5,369,133, 5,369,063 (pore former used to prepare a porous ceramic body), U.S. Pat. No. 5,409,879 (pore forming particles), U.S. Pat. No. 5,413,797 (pore forming agents) and the like. The entire disclosure of each of these United States patents is hereby incorporated by reference into this specification.

The ceramic core 12 should preferably have controllable porosity for use in assays that require sequential penetration of the reactants (dot assays) or capillary migration of the reaction mixture (EIC/LAS) through the solid support. For predictable results, the pore structure of the support should be "open" and be reproducible from batch-to-batch and from site-to-site within the same batch.

In one preferred embodiment, the material from which ceramic core 12 is made is sieved to remove all but a relatively narrow band of particle sizes. Thereafter, this compact is formed into the green body and fired to produce the desired body with the desired pore size distribution.

The ceramic core 12 should have controllable internal capillary migration rates. The phenomenon of capillary migration is well known to those skilled in the art and is discussed, e.g., in U.S. Pat. Nos. 5,334,513, 5,232,835, 5,164,294, 5,156,952, and the like; the disclosure of each of these patents is hereby incorporated by reference into this specification.

As is known to those skilled in the art, the internal capillary migration rate of reactants is dependent upon several factors such as the surface tension of the reaction mixture, the pore size of the solid support, the hydrophobicity/hydrophilicity properties of the internal pore surfaces, the surface charge of the internal pore surfaces, and the like. All of these factors should preferably be controllable in the bioassay to provide a reproducible test environment.

Referring again to FIG. 3, and in the preferred embodiment depicted therein, the sheath 14 has a modulus of rupture of at least about 1,000 pounds per square inch.

A preferred process of the invention

Figure 6:
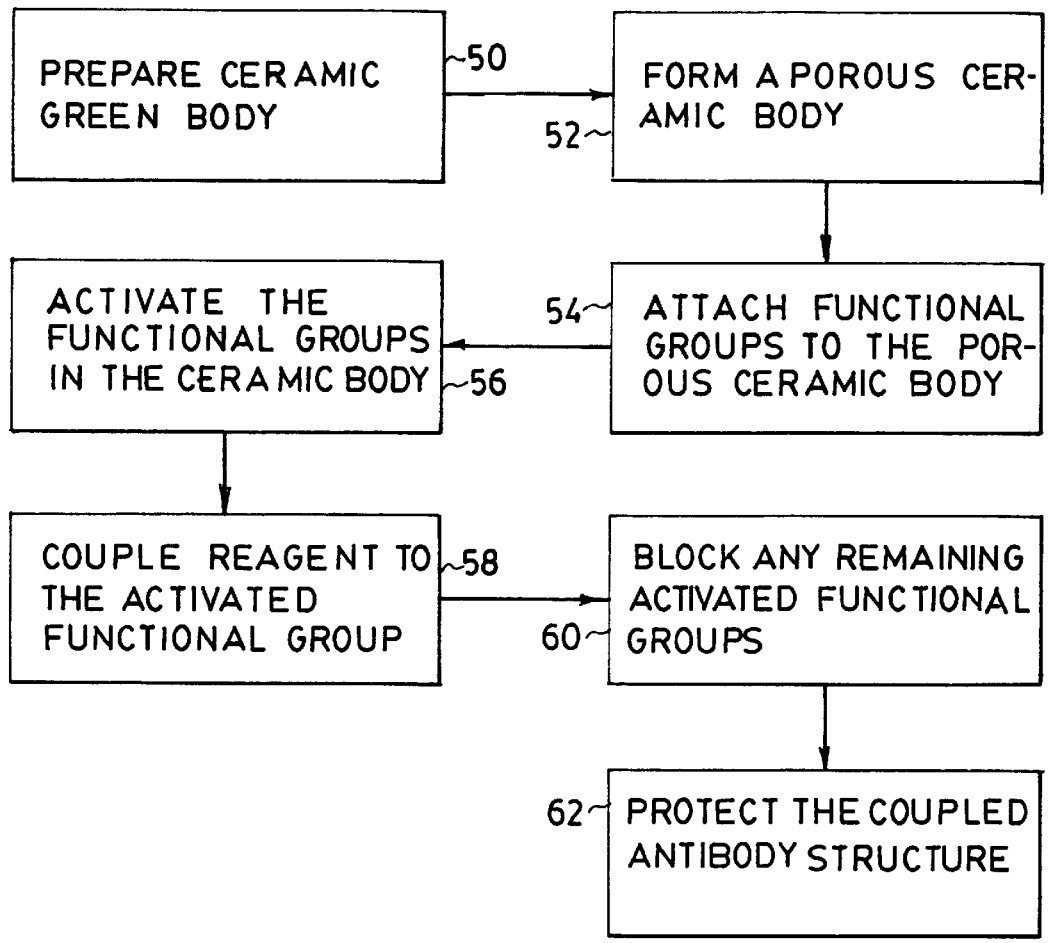
FIG. 6 is a flow diagram illustrating one preferred process of the invention.

FIG. 6 is a flow diagram illustrating one preferred process for preparing a preferred assembly of the invention.

Referring to FIG. 6, and to the preferred process depicted therein, it will be seen that, in step 50, a ceramic green body is prepared.

It is preferred that ceramic core 12 of the assay assembly be a porous ceramic material which is dimensionally stable, changing less than about 0.5 percent under ambient conditions over a period of 1 year.

One preferred ceramic composition is porous glass, which may be made by conventional means. See, e.g., U.S. Pat. No. 5,411,928 (porous glass made by a sol gel process), U.S. Pat. No. 5,371,989 (porous glass mat), U.S. Pat. No. 5,354,428 (forming a porous glass soot body), U.S. Pat. No. 5,340,651 (hydrophilic porous glass fiber), U.S. Pat. No. 5,336,889 (porous glass matrix), U.S. Pat. Nos. 5,262,365, 5,250,095 (glass soot particles), U.S. Pat. No. 5,238,481 (porous glass with interconnective pores), U.S. Pat. No. 5,203,899 (porous glass soot body), U.S. Pat. No. 5,200,374 (transparent porous glass), U.S. Pat. No. 5,186,838 (porous glass chomatographic support), U.S. Pat. Nos. 5,167,822, 5,162,939, 5,116,400, 5,100,841, 5,009,688, 4,966,613, 4,810,674 (porous glass monolith), U.S. Pat. No. 4,780,369 (porous glass membrane tubes), U.S. Pat. No. 4,748,121 (porous glass fibers with immobilized biochemically active material), U.S. Pat. No. 4,707,173 (porous glass rod), U.S. Pat. No. 4,473,476 (porous glass membrane), U.S. Pat. No. 4,042,359 (porous glass membrane tubes), U.S. Pat. No. 3,904,422 (porous glass support material), U.S. Pat. No. 3,881,944 (porous glass/ceramic bodies for catalyst supports), U.S. Pat. No. 3,807,719 (adsorbing and crosslinking enzymes within the pores of porous glass), U.S. Pat. No. 3,792,987 (porous glass support material), U.S. Pat. No. 3,790,475 (porous glass support material), and the like. The disclosure of each of these United States patents is hereby incorporated by reference into this specification.

In one embodiment, the porous glass contains at least about 80 weight percent of silica.

In one preferred embodiment, the material comprising core 12 is porous ceramic material. By way of further illustration of such materials, reference may also be had to U.S. Pat. No. 5,441,581 (alumina porous ceramic), U.S. Pat. No. 5,439,624 (sol gel process), U.S. Pat. Nos. 5,437,832, 5,423,973 (structure with two porous ceramic layers), U.S. Pat. No. 5,416,795 (alumina and silica porous ceramics), U.S. Pat. Nos. 5,415,891, 5,405,529, 5,391,338 (porous ceramic green body formed from casting slip), U.S. Pat. No. 5,384,290 (use of foamable prepolymer to produce porous ceramic), U.S. Pat. No. 5,384,200 (yttria and zirconia porous ceramics), U.S. Pat. No. 5,382,396 (porous ceramic formed by sponge burn out), U.S. Pat. No. 5,385,910 (use of silicon carbide and organopolysiloxanes to form porous ceramics), U.S. Pat. No. 5,328,783 (self supporting porous ceramic plate), U.S. Pat. No. 5,322,821 (use of foamable prepolymer to form a porous ceramic), U.S. Pat. No. 5,322,116 (porous ceramic foam material), U.S. Pat. No. 5,318,755 (porous ceramic with pore size of from 0.04 to 0.5 microns), U.S. Pat. No. 5,310,575 (magnesium spinel porous ceramic material), U.S. Pat. No. 5,308,454 (metal oxide porous ceramic layer), U.S. Pat. No. 5,299,736 (container with porous ceramic walls), U.S. Pat. No. 5,298,205 (use of organic sponge burn out to produce porous ceramic), U.S. Pat. Nos. 5,279,737, 5,275,759 (zirconia sol), U.S. Pat. No. 5,262,199 (alumina coated on silicon carbide porous ceramic), U.S. Pat. Nos. 5,236,151, 5,229,102 (porous ceramic membrane), U.S. Pat. No. 5,227,342 (process of making porous ceramic material with controlled porosity), U.S. Pat. No. 5,205,996 (porous ceramic structure with interconnecting, open pores), U.S. Pat. No. 5,196,238 (porous ceramic compact), U.S. Pat. No. 5,185,110 (cordierite porous ceramic), U.S. Pat. No. 5,183,608 (use of water-insoluble cellulose to prepare porous ceramic) U.S. Pat. No. 5,177,035 (use of curable resin to make porous ceramic), U.S. Pat. No. 5,171,449 (use of crosslinked polyvinyl alcohol to prepare porous ceramic), U.S. Pat. No. 5,104,4\539 (metal oxide porous ceramic), U.S. Pat. No. 4,891,174 (microcellular porous ceramic), U.S. Pat. No. 4,695,301 (porous ceramic monolith), U.S. Pat. No. 4,596,574 (biodegradable porous ceramic), U.S. Pat. No. 4,258,099 (silica porous ceramic bodies), U.S. Pat. No. 4,071,369 (porous ceramic made from expanded clay), U.S. Pat. No. 3,881,944 (porous glass ceramic), U.S. Pat. No. 3,833,386 (porous ceramic from polyurethane foam), U.S. Pat. No. 3,812,050 (use of dextrin to make porous ceramic), and the like. The disclosure of each of these United States patents is hereby incorporated by reference into this specification.

In one embodiment, the ceramic material consists of or is comprised of an oxide material. One preferred oxide material is silicon oxide (such as silica); and in one embodiment the ceramic composition is comprised of at least about 50 weight percent (and, more preferably, at least 80 weight percent) of silica.

Another preferred ceramic composition consists of, or is comprised of, two or more oxide materials. One preferred aspect of this embodiment is clay, which typically includes oxides of metals (such as aluminum, titanium, iron, calcium, magnesium, potassium, sodium and silicon), either in combined and/or noncombined forms.

In one embodiment, a clay is used which comprises at least about 50 weight percent of silicon oxide, $Si(O)_x$ wherein x is from about 1 to about 3. These clays are well known to those skilled in the art and are disclosed, e.g., in Ralph E. Grim's "Clay Mineralogy", Second Edition (McGraw-Hill Book Company, New York, 1968).

Most of these clays contain at least fifty percent of silica and from about 20 to about 40 weight percent of alumina. Thus, by way of illustration, some suitable silica-containing clays include the following clays sold by the H. C. Spinks Clay Company of Paris Tennessee: Black Charm clay (which contains 60.9 percent of silica, 25.5 percent of alumina, and 1.6 percent of titania), New Foundry Hill Creme clay (which contains 59.4 percent of silica, 25.6 percent of alumina, and 1.4 percent of titania), Ven Blend clay (6.1.5 percent silica, 22.8 percent of alumina, and 1.7 percent of titania), SPCT #1 clay (which contains 62.5 percent of silica, 22.8 percent of alumina, and 1.8 percent of titania), Flo-Tech Slurry (which contains 61.5 percent of silica, 22.9 percent of alumina, and 1.7 percent of titania), Spinks Blend clay (which contains 60.2 percent of silica, 24.4 percent of alumina, and 1.5 percent of titania), C&C clay (which contains 58.5 percent of silica, 25.7 percent of alumina, and 1.6 percent of titania), and Tile Blend #2 clay (which contains 62.4 percent of silica, 23.5 percent of alumina, and 1.4 percent of titania).

One family of natural clay is kaolinite, which may be represented by the formula $Al_4Si_4O_{10}(OH)_8$. The kaolinite clays include, e.g., kaolinite, halloystie, dickite, and illite. Reference may be had, e.g., to U.S. Pat. Nos. 5,441,877, 5,403,035, 5,292,360, 5,223,464, etc.

Another family of natural clays is montmorillonite, which may be represented by the formula $(Al,Mg,Fe)_2(Si_2O_5)_2(OH)_2$. See, e.g., U.S. Pat. Nos. 5,421,291, 5,376,283, 5,368,692 (bentonite), U.S. Pat. Nos. 5,352,857, 5,328,682, 5,308,808, 5,303,676, 5,292,992, 5,262,562, and the like.

Another family of natural clays is illite, which may be represented by the formula $(K,Na)_x(Al,Mg,Fe)_2(Al_xSi_{4-x})O_{16}$. See, e.g., U.S. Pat. Nos. 5,288,695 and 3,563,724.

One preferred ball clay, which may be used in the invention, may be purchased from the Kentucky-Tennessee Company of Mayfield, Ky. (as "clay-1").

Referring again to FIG. 6, in step 50 a green body may be formed by conventional ceramic forming methods such as, e.g., by injection molding, slip casting, machining from precast monoliths, cold pressing, etc. See, e.g., James S. Reed's "Principles of Ceramic Processing", Second Edition (John Wiley & Sons, Inc., New York, 1995).

One preferred forming method is to produce a casting slip which is preferably comprised of clay or metal oxide and a volatilizable material, such as talc or calcium carbonate. The casting slip, which also contains a suitable liquid, is poured or extruded into a mold, the liquid is removed from the mold, and a green body which conforms to the shape within the mold is formed. Thereafter, during firing, the volatilization of the volatile material in the green body produces a porous structure.

When forming the green body by slip casting, one may preferably use water, buffered aqueous solutions, salt solutions, or alcohols as the liquid in the casting slip. The casting slip is frequently in the form of a slurry, with its components dispersed within the liquid but not necessarily soluble in the liquid.

One can purchase a pre-mixed casting slip for use in the process of the invention. Thus, e.g., one can purchase "Major Slip" from Bercher Ceramic Supplies of Oklahoma City, Okla.

The mold(s) used in the slip casting process may be prepared by well-known, conventional means.

Thus, for use in the casting process, a positive mold can be prepared with the same shape and size as the item to be cast; see, e.g., U.S. Pat. Nos. 5,376,507, 5,376,506, 5,352,043, 5,298,213, 5,275,987, 5,197,874, 5,168,081. By way of illustration, this shape can be placed within a container and cemented into place. The interior of the container and the positive shape may be sprayed 8–10 times with clear glaze compound. After the glaze is completely dry, the interior of the container and the positive shape may be coated with a 50 weight percent aqueous solution of Ivory dishwashing liquid.

By way of further illustration, a negative mold can be prepared by mixing plaster of Paris with water in a 50/50 weight/weight ratio; see, e.g., U.S. Pat. Nos. 5,298,213, 5,194,204, and 5,169,577. The plaster slurry can then be poured into the container with the positive mold and allowed to react for 30 minutes at room temperature. The negative impression mold of the object may then removed from the positive mold container and allowed to dry thoroughly over a period of from about 3 to about 5 days.

Referring again to FIG. 6, and to step 52 thereof, after the ceramic green body has been formed, a porous ceramic body is then formed. Pores in the ceramic composition may be formed by inclusion of one or more pore-forming materials in the green body at the time it is cast, extruded, or otherwise formed. The amount of porosity created in the ceramic material will depend, at least in part, on both the concentration of the pore-forming material in the ceramic matrix and, also, on the particle size distribution of the pore-forming material.

It is preferred that the ceramic green body comprise from about 20 to about 60 volume percent of the pore-forming material and, more preferably, from about 30 to about 45 volume percent of the pore-forming material. In an even more preferred embodiment, from about 38 to about 42 volume percent of the pore-forming material is used.

Referring again to FIG. 6 (see step 52), prior to firing, the green body may be treated to insure that, after firing, certain of its surfaces will have a different amount of porosity than other of its surfaces. This can be done by applying glaze to those surfaces which one desires have a lower degree of porosity. Alternatively, or additionally, a non-porous substrate may be bonded to those surfaces for which a lower porosity is desired.

Thus, for example, glaze-resistant wax may be applied to all of those areas of the green body which are not to be glazed and allowed to soak into the green body; glaze is then applied to the non-waxed surfaces of the green body; and, during the subsequent firing step, the wax will burn off. If desired, markings may be applied to the green body at this time. A suitable glaze resistant wax which may be used includes, e.g., "Wax Resist", which is sold as catalog number SY547 by the Duncan Corporation of Fresno, Calif.

A glaze is any material which can be used to seal the surface of the green body. Thus, glazes include, e.g., waxes, shellacs, varnishes, and glasses.

A clear glaze can be formed by coating the green body with a suspension of finely ground glass which fires to a clear, non-porous glaze coating. A suitable clear glaze which may be used includes, e.g., "Infinity Glaze—Clear", which is sold as catalog number IN1001 by the aforementioned Duncan Corporation.

Opaque glazes can be formed by coating the green body with a suspension of finely ground glass, limestone, talc, or other finely ground (particle size less than 100 microns) oxides of silicon or aluminum.

The glaze(s) may be applied by painting, spraying, dipping, or other conventional techniques, either prior to firing, or after the green body has been preliminarily fired.

Non-glazed areas may be protected from the glaze by physical masking with an agent such as, e.g., such "Wax Resist". Alternatively, as is illustrated in FIGS. 4 and 5, the shape of the body contacted with the glaze may prevent certain areas from being coated. Other conventional masking means also may be used.

Gradations or other markings, in the form of numbers or letters formed of colored glass particles on a decal backing, can be applied to the glaze. The structure may then be fired to fuse the decal backing, leaving the numbers and gradations on the glaze.

The firing temperature used generally is from about 800 to about 2,000 degrees Centigrade. Thus, e.g., where ball clay and talc are used to form the green body, it is preferred to use a temperature of from about 1,000 to about 1,200 degrees Centigrade.

Referring again to FIG. 6, and in the preferred embodiment illustrated in step 54 of FIG. 6, functional, reactive groups are preferably attached to molecules within the porous ceramic body.

These functional, reactive groups, and/or reagents coupled to the ceramic material, may be attached to the ceramic material by conventional means. Thus, e.g., reference may be had to U.S. Pat. No. 4,071,409 of Messing et al. (coupling to a titanium oxide support), U.S. Pat. No. 4,059,685 of Johnson (coupling to a metal oxide support), U.S. Pat. No. 3,912,593 of Barker et al. (coupling to a metal support), U.S. Pat. No. 4,425,438 (coupling to a support made of cellulose, polypropylene, or chromium oxide), U.S. Pat. No. 5,273,908 of Sakata et al.(coupling to a support made of plastic, silicone, or alumina), U.S. Pat. No. 5,272,094 of Barker et al. (coupling to a support made of polymer or metal oxides), U.S. Pat. No. 5,268,306 to Berger et al. (coupling to a polymeric support, such as a carbohydrate), U.S. Pat. No. 5,137,827 to Mroczkowski et al. (coupling to a plastic support, a glass support, or a polystyrene support), U.S. Pat. No. 5,079,155 of Cox et al. (coupling to a fluorocarbon polymer support), U.S. Pat. No. 4,885,207 of Johnson et al. (coupling to a silica, alumina, or zirconia support), U.S. Pat. No. 4,775,619 of Urdea (coupling to polysaccharides, polystyrene, glass, or ceramics, U.S. Pat. No. 4,363,634 of Schall, Jr. (coupling to glass, ceramic, metal, or wood), and the like. The disclosure of each of these United States patents is hereby incorporated by reference into this specification.

It is preferred that support material used have easily modifiable functional groups, such as $-NH_2$, $-OH$, $-SH$, $-COOH$, and $=$groups, for coupling; and, in step 54 of the process of this invention, such functional groups may be attached to the support; alternatively, one or more of these groups may inherently exist within the support material. These amino, sulfhydryl, carboxyl and aldehyde groups are desirable because reagents are available for activation in preparation for coupling to protein and carbohydrate ligands.

The concentration and identity of any of the aforementioned functional groups within the ceramic core 12 may be determined by conventional qualitative and quantitative analytical methods; see, for example, John P. Sibilia "A Guide to Materials Characterization and Chemical Analysis" (VCH Publishers, Inc., 220 East 23rd Street, Suite 909, New York, N.Y.). Thus, by way of illustration, the concentration of hydroxy groups within the ceramic may be determined by contacting the ceramic with trimethoxysilane and measuring the amount of methanol produced.

It is also preferred that the support material have evenly distributed functional groups for ligand coupling. Evenly distributed functional groups are important for the preparation of bioassay materials to prevent inter- and intra-batch variability.

The reagents to be coupled to the support material are preferably biologically active molecules which are specifically reactive with analyte and/or a second reagent which is usually labeled and which is freely diffusible within the ceramic composition. The reagents can be attached to the support material via coupling or functional groups.

As used herein, the term biologically active molecule refers to a molecule which is one half of a specific binding pair of molecules which, because of their respective stereochemistries, fit together in a "lock and key" pattern and preferentially react with each other. The biologically active molecules of interest in this invention fit in such "lock and key" pattern with the analyte to be measured by applicants' assay device.

Some preferred biologically active molecules include proteins, such as antibodies, enzymes, hormones, receptors, and other portions of diagnostic utility.

Polysaccharides are useful biologically active molecules. Thus, by way of illustration, one may use polysaccharides such as the glycosylated moieties unique to receptors such as P-selectin, heparin, and various lectins.

Nucleic acid sequences may also be used, such as primers for the polymerase chain reaction, complementary oligonucleotides, and other nucleic acid sequences specifically reactive with a target substrate, which are useful, directly or indirectly, for the purpose of detecting or measuring other molecules.

In one embodiment, the ceramic material contains from about 0.01 to about 1.0 weight percent of biologically active molecules such as, e.g., protein molecules. The identity and presence of these molecules may be determined by conventional means. Thus, by way of illustration, one may use one or more of the protein assay kits disclosed on page 144 of the 1993 "BioTech Buyers' Guide" (American Chemical Society, Washington, D.C.)

In the next section of the specification, reference will be made to the derivatization of a ceramic support material, it being understood that other support materials (such as porous plastic, porous paper, agarose gels, and the like) can also be derivatized in a similar manner and used as porous supports.

Methods for coupling and/or immobilizing biologically active molecules and/or materials onto and within high surface area inorganic supports are well known to those skilled in the art and may be used in the process of this invention.

Thus, by way of illustration, reference may be had to U.S. Pat. No. 3,519,538 (enzymes coupled via intermediate silanes to various inorganic), U.S. Pat. No. 3,556,945 (enzymes adsorbed to porous glass), U.S. Pat. No. 3,652,761 (antibodies coupled via silanes to various inorganics) U.S. Pat. No. 3,804,719 (enzymes cross-linked within the pores of porous glass), U.S. Pat. No. 3,839,175 (enzymes immobilized via electrodeposition within the pores of various ceramics), U.S. Pat. No. 3,850,751 (enzymes absorbed within the pores of various ceramics), U.S. Pat. No. 3,930,951 (enzymes coupled via BMBD to inorganic), and the like. The disclosure of each of these United States patents is hereby incorporated by reference into this specification.

By way of further illustration, an electrical immunoassay technique which utilizes field effect transistors coated with a layer of antibody in the gate region is known to those in the art. If an antigen-antibody reaction occurs, the charge concentration of the transistor changes. Reference may be had to U.S. Pat. Nos. 4,238,757, 4,180,771, 4,334,880, and 4,444,892. The entire disclosure of each of these United States patents is hereby incorporated by reference into this specification.

By way of further illustration, U.S. Pat. No. 3,966,897 of Renn et al. discloses that porous glass substrates may be activated with p-isothiocyanato-phenoxy hydroxy propyl chloride and thereafter coupled with the antibody associated with hepatitis (HB Ab) or, alternatively, the antibody containing an indicator dye which is disclosed in U.S. Pat. No. 3,641,235. The disclosure of each of these patents is hereby incorporated by reference into this specification.

By way of further illustration, in U.S. Pat. No. 4,024,235 Weetall et al. describe a method for bonding biomaterials directly to glass or ceramic supports by incorporating derivatives of silane compounds onto the silaceous surfaces of a support. The disclosure of this patent is hereby incorporated by reference into this specification.

By way of yet further illustration, U.S. Pat. No. 4,059,685 of Johnson discloses a mass of porous refractory particles having a water insoluble polymer (such as dextran) bonded to it. The polymer has bonded to it antibodies capable of binding a specific antigen. The disclosure of this patent is hereby incorporated by reference into this specification.

By way of further illustration, U.S. Pat. No. 4,071,409 of Messing et al. discloses a method of bonding biologically active proteins (such as enzymes or antibodies) to an inorganic support having surface hydroxyl or oxide groups (such as titania, alumina, silica, or glass) in which the inorganic support is reacted with an organic solution of a polymeric isocyanate with a molecular weight of at least about 250. The disclosure of this patent is hereby incorporated by reference into this specification.

By way of further illustration, U.S. Pat. No. 4,363,634 of Schall discloses a process in which a porcelain material is coated with polymer to which a polypeptide glycoprotein is thereafter adsorbed. The disclosure of this patent is hereby incorporated by reference into this specification.

In David Bauman's U.S. Pat. No. 4,425,438, disclosure is made of the coupling of coccidiodes immunodiffusion antigen to glass beads. The disclosure of this patent is hereby incorporated by reference into this specification.

U.S. Pat. No. 4,735,906 of Bastiaans et al. discloses an immunosensor using surface acoustic waves on a piezoelectric quartz crystal. An antibody is immobilized onto the quartz surface using commonly available organosilane coupling reagents. The disclosure of this patent is hereby incorporated by reference into this specification.

U.S. Pat. No. 5,079,155 discloses a fluorsurfactant-treated fluorosilane-coated porous silica-based support. The disclosure of this patent is hereby incorporated by reference into this specification.

By way of further illustration, U.S. Pat. No. 4,775,619 of Urdea discloses a process for binding a label to a support (such as glass) wherein, on cleavage of either a single or double strand, the label may be released from the support and the release can be detected as indicative of the presence of a particular oligonucleotide sequence. The disclosure of this patent is hereby incorporated by reference into this specification.

U.S. Pat. No. 4,885,207 of Johnson et al. discloses the coating of a titania or titanated alumina with a polymeric alcohol (such as polyvinyl alcohol) which is thereafter cross-linked and converted, at least in part, to sulfonate-ester structures. The thus coated support is bound to enzymes and/or antibodies. The disclosure of this United States patent is hereby incorporated by reference into this specification.

U.S. Pat. No. 5,187,066 of Becker et al. discloses the preparation of octyltrichloro-silane glass beads. The disclosure of this patent is hereby incorporated by reference into this specification.

By way of further illustration, U.S. Pat. No. 5,273,908 discloses the preparation of antiinsulin antibody-bound glass substrate. The disclosure of this patent is hereby incorporated by reference into this specification.

By way of further illustration, in a publication by Weetall, Biochem. Biophys. Acta. 212 (1970) 1–7, a process was disclosed in which glass was treated with gammaaminopropyltriethoxysilane and the iosthiocyanate derivative was prepared by treatment with thiophosgene. An enzyme was coupled to the iosthiocyanate derivative.

Furthermore, in the aforementioned Weetall publication, there also was described the preparation of an arylamine derivative by the reaction of alkylamine glass with P-nitrobenzoyl chloride followed by the use of sodium dithionate to reduce the nitro groups. The arylamine glass was then diazotized and an enzyme coupled thereto.

By way of further illustration, Weetall, in Biochem. J. (1970), 117, 257–261 describes the use of antibodies bound to porous glass through a silane coupling agent, the immunoadsorbent being used to isolate and purify specific antigens.

As will be apparent to those skilled in the art, different methods for coupling reagents to the ceramic support material can be used, depending on the chemical composition of the ceramic and the chemical nature of the reagent to be attached to the ceramic composition. These methods include, e.g., cyanogen bromide coupling, silation, diazo coupling, carbodiimide coupling, as well as others known to those skilled in the art.

In cyanogen bromide coupling, proteins and polysaccharides can be coupled onto supports having coupled thereto appropriate reactive groups, such as, e.g., hydroxyl and/or aldehyde groups. It can also be used for the introduction of spacer groups such as diaminoalkyl groups containing from 3 to about 20 carbon atoms, or diaminoaryl groups containing from 6 to 20 carbon atoms, or gammaaminoalkyl groups, or aryl carboxylic acid moieties, onto the support. Reagents for this process are commercially available.

By way of further illustration, the ceramic composition may be derivatized with functional groups by infiltration of ceramic pores with functional groups attached to trimethoxysilanes or triethoxy silanes. This is preferably accomplished by applying a vacuum to the ceramic composition and then releasing the vacuum while the composition is immersed in the silane.

By way of illustration, where one wishes to attach an amino group to the porous ceramic material, one may use amino-propyl-trimethoxysilane as the derivatizing agent. Thus, e.g., 3-aminopropyltrimethoxysilane may be purchased as reagent 28,177-8 from the Aldrich Chemical Corporation of 1001 West Saint Paul Avenue, Milwaukee, Wis. (see, e.g., the 1992–1993 Aldrich catalog).

The amino-propyl-trimethoxysilane (APTMS) can be diluted to a concentration of about 80 volume percent with distilled water. The solution can then be incubated at room temperature for from about 1 to about 2 hours to allow the silane to hydrate.

The ceramic support material can then be placed in the APTMS solution, and the assembly can then be placed in a vacuum chamber. The assembly can then be subjected to a vacuum of at least about 200 milliTorr of mercury to remove air from the pores of the ceramic composition and to cause the silane solution to diffuse into such pores. Thereafter, the ceramic support material can be is removed from the silane solution.

The ceramic support material can then be placed onto an absorbent pad and subjected to a vacuum of at least about 100 milliTorr of mercury to remove excess solution. Thereafter, the vacuum on the support material can be released, and the support can be dried (preferably in an oven at a temperature of at least about 100 degrees Centigrade) for at least about 30 minutes, or until the support material contains less than about 1 percent of liquid.

Other trimethoxysilanes and triethoxysilanes can be used to attach other functional groups to the ceramic material. These alkoxysilanes are well known to those skilled in the art. Thus, referring to pages 199–202 of "Classes of Compounds and Numerical Cross Reference List", which is a "Supplement to the 1988–1989 Aldrich Catalog . . . ", alkoxysilanes include allyltriethoxysilane, 3-aminopropyltriethoxysilane, 3-aminopropyltrimethoxysilane, t-butyldiphenylmethoxysilane, chloromethyl(diisopropoxy) methylsilane, 3-chloropropyltrimethoxysilane, dimethoxymethylphenylsilane, ethoxytrimethylsilane, 3-glycidoxypropyltrimethoxysilane, (3-mercaptopropyl) trimethoxysilane, methyltriacetoxysilane, methyltriethoxysilane, methyltrimethoxysilane, trimethoxysilane, and the like. Although not all of these groups will necessarily have the desired degree of reactivity and/or the desired functional group(s), they can be modified by conventional synthetic chemical means to produce trialkoxy silanes with the desired properties.

Various triethoxysilanes and trimethoxysilanes may be used for silation. By way of illustration and not limitation, gammaaminopropyltriethoxysilane, or N-(beta-aminoethyl-gamma-aminopropyl)trimethoxysilane spacer groups can be attached. Thus, e.g., a 80 volume percent solution of the triethoxy- or trimethoxysilane can be prepared with water. The ceramic support may then be immersed in the solution and permeated by vacuum or suction. The support may then be washed by intermittent vacuum with acetone, followed by water, in order to remove excess silane.

Referring again to step 56 of FIG. 6, amino groups, after they have been attached to the ceramic, can be activated with glutaraldehyde. Glutaraldehyde (CAS Reg. 111-30-8) is readily commercially available and may be obtained, e.g., as reagent G151-1 from Fisher Scientific, 711 Forbes Avenue, Pittsburgh, Pa.

Thus, by way of illustration, in order to activate the amino groups a solution of 0.02 percent of glutaraldehyde may be prepared in a sodium carbonate/sodium bicarbonate buffer. The silane-coated ceramic support may be immersed in the glutaraldehyde solution, and the assembly may then be subjected to a vacuum of at least about 200 milliTorr to cause the glutaraldehyde solution to migrate into the pores of the ceramic support. Thus, by way of further illustration, and in one particular embodiment, in order to activate the amino groups in the porous ceramic material a 1.25 percent solution of glutaraldehyde is prepared in a phosphate buffer with a pH of 6.8. The glutaraldehyde is applied to the porous ceramic material, preferably with a syringe or a needle. The ceramic assembly is then incubated for from about 30 to about 120 seconds at room temperature. Then an air knife or an air jet is used to remove the solution from the pores of the porous ceramic material.

The ceramic assembly is then washed. A 0.1 molar solution of carbonate/bicarbonate with a pH of 9.5 is first applied to the assembly, and an air knife or air jet is then used to remove the solution from the pores of the ceramic material. This sequence is then repeated two more times to complete the washing cycle.

A protein solution with the molecules one desires to couple to the ceramic material is then applied to the washed, porous ceramic material. In one preferred embodiment, the protein solution applied is a estrone sulfate antibody, which may be more particularly described as a murine monoclonal (isotype LgG-1) generated against estrone-3-glucunoide conjugated to human globulins. This antibody, which may be purchased from the AgResearch Wallaceville Animal Research Centre of Ward Street, Upper Hutt, New Zealand, exhibits substantial cross-reactivity against estrone, estrone sulfate, and estrone glucuronide.

After the protein solution has been applied to the porous ceramic material, the assembly is incubated for from about 15 to about 150 seconds at room temperature. Thereafter the incubated assembly is washed with a 0.1 molar phosphate buffer which has a pH of 6.8 and contains 0.01 molar of ethanolamine or methanolamine, and an air knife or air jet is then used to remove solution from the pores of the ceramic material. This washing/removal sequence is then repeated once.

Thereafter, a solution of 0.1 molar ethanolamine in 0.1 molar phosphate buffer solution (pH 6.8) is applied to the porous ceramic material and incubated.

In the final washing sequences, an air knife or an air jet is used to remove solution from the pores of the ceramic material, the ceramic assembly is then washed with deionized water, the excess water is removed with an air knife or an air jet, and a 20 percent solution of sucrose in deionized water is then applied to the assembly; the excess sucrose is not removed from the pores of the assembly. At this point, the assembly may be freeze dried to preserve it for further use.

The washed assembly is then again washed with a 20 percent solution of sucrose in deionized water Thereafter, the vacuum may then be released and the ceramic pieces removed from the solution. The coated pieces can then be placed onto an absorbent pad and returned to the vacuum chamber, wherein they are again subjected to a vacuum of at least about 200 milliTorr.

Without wishing to be bound to any particular theory, applicants believe that activation of an amine involves formation of a Shiff's base.

By way of further illustration, carboxyl, hydroxyl, and/or aldehyde functional groups are preferably activated with carbodiimides. Applicants believe that subsequent reaction of the carbodiimide activated groups with biologically activated materials containing a free amine involves formation of a peptide bond.

By way of further illustration of a particular procedure involving coupling, carbodiimide coupling of proteins and amine-containing organic molecules to spacer groups or supports or particles also may be used. Thus, e.g., in one instance, the terminal amine of the support bound spacer may be converted to a carboxylic acid by treatment with a solution containing 9.5 molar succinic anhydride with incubation at 25 degrees Centigrade for 12–18 hours while maintaining the pH at 7–8. The support may then be washed by filtration with water. The support-bound carboxylic acid spacer is then incubated with 0.1 molar 1-(3-dimethylaminopropyl)-3-ethylcarbodiimide at pH 5 and a temperature of 2–8 degrees Centigrade for 4 hours. The protein or amine-containing molecule is then washed in 0.1 molar phosphate buffer containing 0.15 molars sodium chloride (pH of 7.5)) and added to the support by the procedure described elsewhere in this specification. The support is then incubated at 2–8 degrees Centigrade for 12–18 hours, and unbound material is removed.

By way of further illustration, carbodiimide coupling of organic molecules containing caroboxyl or aldehyde groups to spacer groups on supports also may be used. Thus, e.g., the support bound spacer may be suspended in a solution containing 0.1 molar 1-(3-dimethylaminopropyl)-3-ethylcarbodiimide. The organic molecules are then dissolved in 0.15 molar sodium chloride solution at a pH of 5.0 and added to the support mixture. The support is then incubated at 2–8 degrees Centigrade for 12–18 hours, and unbound materials are then removed. By way of further illustration, glutaraldehyde coupling of proteins and other amine-containing molecules to spacer groups on supports also may be used. Thus, e.g., the support bound spacer groups may be incubated with a freshly prepared solution containing 0.5 volume percent of glutaraldehyde in water for 20 minutes at room temperature. The support is then washed by filtration with water. The support bound spacer is then added to a solution containing the protein or molecules to be coupled in 0.15 molar sodium chloride solution. The support is then incubated at room temperature for 2 hours, and unbound material is then removed.

In one preferred embodiment, antibody is coupled to the porous ceramic support material. This may be done in accordance with the procedure described hereinafter.

A solution of reagent, such as antibody, is prepared in a carbonate/bicarbonate buffer at a pH of 9.0. Thus, by way of illustration, one may use monoclonal antibody Apolipoprotein (APD B-100), which may be purchased from Fitzgerald Industries International of Concord, Ma. as catalog number 10A15 (clone #M4110321). A solution of such an antibody, at a concentration of 1 microgram per milliliter, may be prepared using a 0.2 molar sodium carbonate/sodium bicarbonate buffer at a pH of 9.

Apolipoprotein B-100 (ALP B-100)is associated with low-density lipoprotein (LDL), elevated levels of which are associated with atherogenesis and coronary artery disease. The assay structures of this invention can be used to readily test for this protein.

A 0.2 molar bicarbonate buffer can be prepared by adding to 0.2 molar sodium carbonate a sufficient amount of sodium bicarbonate to reduce the pH to 9.

A 1 microgram per milliliter solution of the monoclonal antibody in the buffer is prepared.

The derivatized/activated (derivatized) ceramic pieces are then immersed in the solution of antibody. The container is placed in a vacuum chamber, and a 200 milliTorr vacuum is imposed and held for 10 minutes. Thereafter, the vacuum is released to impregnate the ceramic support pieces with the antibody.

After release of the vacuum, the ceramic support pieces are maintained in the buffer at a temperature of from 2 to 8 degrees Centigrade for from 18–48 hours.

The reagent that is immobilized to the ceramic support material is usually not labeled, although it may be in some cases where reaction with an analyte elicits a directly detectable event. In most cases, a second reagent which is freely diffusible within the ceramic composition is labeled, and binding of immobilized reagent with analyte is indirectly detected. In the case of a competitive binding assay, where both analyte and diffusible reagent compete for binding to the immobilized reagent, the physical displacement of labeled reagent is detected directly. In the case of a sandwich assay, binding of analyte to immobilized reagent is detected by binding of labeled reagent to the bound analyte.

Examples of labels which can be coupled to the reagents or analyte include, e.g., dyes, chromogenic substrate-enzymes systems, chemiluminescent compounds and systems, fluorescent compounds, radiolabels, and colored particles. Thus, e.g., metallic sol labels (described in EPA 7654) may be used. Thus, e.g., colloidal gold particles having a diameter of 20 nanometers (sold by Janssen Life Science Products) may also be used. Dye sols are described in EPA 32270 and can be obtained commercially as hydrophobic dyestuffs (such as "Foron Blue SRP" from Sandoz, and "Resolin Blue BBLS" from Bayer). Latex or polymer particles can be formed of polystyrene, polyvinyltoluene, polystyrene-acrylic acid, polyacrolein, and other polymers. Dye is typically encapsulated at the time of particle formation by solvent evaporation, solvent casting, spray drying, or other techniques well known to those skilled in the art.

One preferred colored latex material which may be used can be purchased from Seradyn Inc., Particle Technology Division, 1200 Madison Avenue, Indianapolis, Ind., as "Uniform latex particles PS/BK". These particles have a diameter of 0.075 microns.

In one preferred embodiment, a reagent comprised of this colored latex material is prepared, and this reagent is then added to well 202 (see FIG. 22) after a sample from the animal has been added to such well.

In this embodiment, the colored latex material has coupled to it the antigen to which the antibody in the porous ceramic material specifically reacts. Thus, where one desires to detect estrone sulfate in the sample from the domestic animal, one will also bond estrone sulfate to the colored latex material.

By way of illustration, estrone sulfate may be conjugated to albumen by conventional techniques. Reference may be had, e.g., to Chapter 11 (pages 11-1 to 11-54) of Frederick M. Ausubel et al.'s "Short Protocols in Molecular Biology", Second Edition (John Wiley & Sons, Inc., New York, 1992) for a description of various techniques for preparing and using monoclonal and polyclonal antibodies.

The colored latex material, which is hydrophobic, is mixed with the estrone sulfate material in a glycine buffeed diluent; one suitable diluent,e.g., is comprised of 1000 milliters of deionized water, 2 grams of sodium azide, 7.5 grams of glycine, and 9 grams of sodium chloride; the pH of ths diluent preferably is about 6.8. Because of its hydrophobicity, it absorbs the estrone sulfate material. This modified colored latex material is then ready to use together with applicants' assay assemblies (see the assay assembly 200 depicted in FIG. 22).

The detectable label can be formed by coupling the label (such as the latex particles) to amino groups on the reagent by activating the carboxy groups on the latex particles with 1-(3-dimethylaminopropyl)-3-ethylcarbodiimide, and then by adding the reagent to the activated latex.

Thus, by way of further illustration, the aforementioned, dark blue latex particles can be coupled to purified Apolipoprotein (APOB-100), which may be purchased (as catalog number 30 -AA25) from the aforementioned Fitzgerald Industries International Corporation. Coupling can be effected by both adsorption (hydrophobic bonding) and covalent linkage via carboxy groups. The latex can be activated by the aforementioned carbodiimide.

As will be apparent to those skilled in the art, many other reagents and/or labels may be used with the system. Thus, by way of illustration, some preferred enzymes include horseradish peroxidase, alkaline phosphate, beta-galactoside, and the like. Preferred dyes include amido black and eosin. Preferred fluorescent compounds include fluorescein isothiocyanate and the like. Preferred radioisotopes include Carbon 14 and Iodine 125. Preferred colored particles include colored latex, colored ceramic particles, etc.

By way of further illustration, preferred labels include colloidal gold particles, dye particles, and colored latex particles having a diameter from about 0.01 to about 0.5 microns (and, more preferably, from about 0.05 to about 0.5 microns).

It is preferred, when using a label, to select the porosity of the ceramic so that the particles are able to move freely within the ceramic by diffusion but that surface area is maximized for immobilization of unlabeled reagent, labeled analyte, or unlabeled analyte.

Referring again to FIG. 6, and in the preferred process depicted therein, any non-coupled activated functional groups should be blocked. This is effected in step 60.

After the coupling of the reagent (such as the antibody) to the activated functional groups on the ceramic support pieces, some activated groups may still not be coupled to reagent. They preferably are neutralized prior to use of the device to prevent non-specific binding of other molecules.

Blocking may be effected by conventional means. Thus, by way of illustration, the coupled ceramic material may be submerged in a solution made from 0.15 molar sodium chloride, 0.01 percent sodium azide, and 0.1 percent bovine serum albumen. Many other suitable blocking means will be apparent to those skilled in the art. Thus, one may utilize other inexpensive inert proteins, or other amino-group containing compounds (such as ethanolamine), which will react with any remaining activated sites.

Referring again to FIG. 6, and in step 62 thereof, the coupled antibodies on the ceramic support are then protected from the effects of air oxidation. Thus, e.g., the ceramic supports may be immersed in a sucrose solution. In accordance with the procedure described elsewhere in this specification, excess sucrose may be removed by placing the ceramic support material on an absorbent pad, subjecting it to a vacuum of at least about 200 milliTorr, and then releasing the vacuum.

Without wishing to be bound to any particular theory, applicant believes that the sucrose molecules fill the interstices within the ceramic core 12 and prevent access of air or oxygen thereto.

Thereafter, the sucrose-impregnated samples can be frozen at a temperature of about minus 70 degrees Centigrade. One suitable freezer which may be used for this purpose is a model B10 freezer sold by Forma Scientific Inc. of Mill Creek Road, Marietta, Ohio.

The frozen samples may then be freeze-dried in a suitable lypholizer such as, e.g., the Virtis model 15SRC-X freeze-drier which is sold by the Virtis Company, Inc. of New York. The chamber may be back-filled with nitrogen at the end of the run.

The freeze-dried strips may then be placed into foil bags together with dessicant (such as "Dri-Rite" dessicant pouches) and heat sealed.

Referring again to FIGS. 1, 2, and 3, substantially homogeneously disposed throughout said ceramic core 12 is from about 0.01 to about 1 weight percent of biologically active molecules for the detection of analyte.

In general, the concentration of any particular biologically active molecule within ceramic core 12 is from about 0.01 to about 1 weight percent (by total weight of ceramic core and biologically active molecules). It is preferred that from about 0.01 to about 0.05 weight percent of biologically active molecules be present in ceramic core 12. In an even more preferred embodiment, from about 0.01 to about 0.03 weight percent of biologically active molecule is present in the ceramic core 12.

To determine whether any particular biologically active molecule is substantially homogeneously dispersed in a particular ceramic core 12, the core should be divided into four sections of substantially equal weight, and the concentration of biologically active molecule in each such section then should be determined. Thereafter, the concentration of biologically active molecule per unit weight for each such section is calculated. It is preferred that, in ceramic core 12, the lowest concentration of biologically active molecule per unit weight is at least about 0.95 as great as the highest concentration of biologically active molecule per unit weight.

A similar procedure may be utilized to determine the uniformity of the mean pore size and the porosity characteristics of the ceramic core 12.

Referring again to FIG. 1, there is illustrated one basic structure of the assay assembly 10 as it might be con figured for use in an enzyme immunochromatography/linear assay system (EIC/LAS), a competitive binding displacement assay which is read like a thermometer. Reference may be had to U.S. Pat. No. 4,425,438, the entire disclosure of which is hereby incorporated by reference into this specification.

EIC/LAS is a means by which an analyte can be accurately measured and the result read like a thermometer in a low-cost, single-use-throw-away device which requires no instrumentation. In a typical EIC/LAS, the detectable reagent has the same affinity for an immobilized reagent as does the analyte. The analyte and the detectable reagent therefore compete for immobilized reagent. The higher the concentration of analyte, the greater the distance moved from the point of application of the analyte and detectable reagent, as measured by detection of the detectable reagent.

Figure 7:
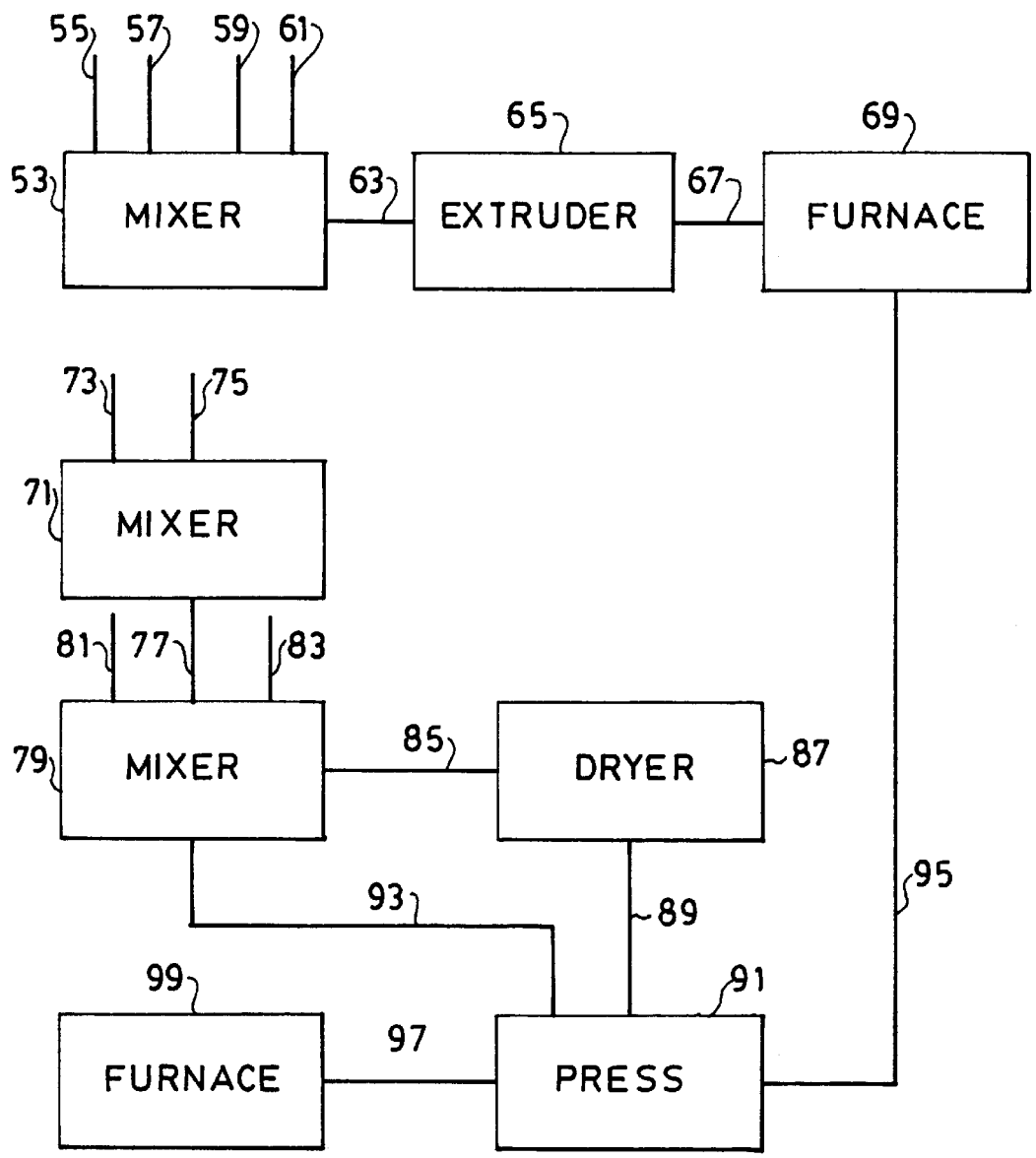
FIG. 7 is a flow diagram illustrating another preferred process of the invention.

FIG. 7 illustrates a preferred process for preparing the support assembly 18 of FIG. 2.

Referring to FIG. 7, an extrusion mixture is prepared in mixer 53.

To mixer 53 is charged, via line 55, from about 85 to about 98 weight percent (by total weight of dry material charged to mixer 53) of calcined alumina.

Calcined alumina is made by calcining aluminum hydroxide. The commercial product is 99.1% alumina with no more than 0.5 percent adsorbed water.

Calcined alumina products are readily commercially available. Thus, by way of illustration, one may use A15 SG calcined alumina sold by Alcoa Industrial Chemicals, Park Lane Drive, Pittsburgh, Pa.

In addition to the calcined alumina, from about 10 to about 15 weight percent of water (by total weight of dry solids charged to mixer 53) may be charged via line 57. In one embodiment, it is preferred to charge from about 11 to about 13 weight percent of water.

In addition to the calcined alumina and the water, from about 0.25 to about 3.0 weight percent (by total weight of dry material) of a binder is charged via line 59 to mixer 53. Suitable binders are well known to those skilled in the art and are described, e.g., on pages 172–182 of James S. Reed's "Principles of Ceramic Processing", Second Edition (John Wiley & Sons, Inc., New York, N.Y., 1995).

One preferred class of binders which may be used is the cellulose ether binders, which include methyl cellulose, hydroxymethylcellulose, sodium carboxymethylcellulose, and the like. Thus, e.g., one may charge from about 1 to about 2 weight percent of "Methocel F4M" binder (which is sold by the Dow Chemical Company of Midland, Mich.) via line 59.

In addition to the calcined alumina, the water, and the cellulose ether binder, one may also charge from about 2 to about 8 weight percent (by total weight of dry solids charged) of a film-forming binder wax via line 61. These binder waxes are discussed, e.g., on pages 181–182 of the aforementioned James Reed book.

In one preferred embodiment, from about 4 to about 6 weight percent of "Mobilcer C" wax (which is sold by the Mobil Chemical Corporation) is used.

Referring again to FIG. 4A, after the materials in mixer 53 have been thoroughly mixed to produce a substantially homogeneous product, this mixture is charged via line 63 to extruder 65, in which a green body in the shape of sheath 14 is formed.

One may use any of the conventional extruders to prepare a green body of sheath 14. Thus, by way of illustration, one may use one or more of the devices described on pages 450–476 of the aforementioned Reed book. Thus, e.g., one may use a Loomis piston-type hydraulically-actuated extruder equipped with a steel die.

The green body produced in extruder 65 generally shrinks from about 10 to about 20 percent when it is fired. Thus, the steel die in the extruder should be designed so that the green body it produces is from about 10 to about 20 percent larger than the desired dimensions for the fired body.

Referring again to FIG. 7, the green body produced in extruder 65 is passed via line 67 to furnace 69. In furnace 69 the green body is subjected to a temperature of from about 1,550 to about 1,750 degrees centigrade for from about 2 to about 4 hours. It is preferred to subject the green body to a temperature of from about 1,625 to about 1,675 degrees Centigrade for from about 2.5 to about 3.5 hours. After the body has reached its desired density, it is allowed to cool.

In a separate mixing operation, a binder composition is prepared in mixer 71. This binder composition is prepared by mixing from about 60 to about 80 weight percent of nepheline syenite and from about 20 to 40 weight percent of ball clay.

Nepheline syenite (also known as nephelite syenite) is a mineral aggregate consisting chiefly of albite, microcline, and nephelite; see, e.g., A.S.T.M. C242-60. It is preferred to use from about 65 to about 75 weight percent of this nepheline syenite.

In addition to nepheline syenite, the binder also preferably contains from about 25 to about 35 weight percent of ball clay.

One may use many of the commercially available ball clays to prepare the binder. Thus, by way of illustration and not limitation, one may use "Black Charm" clay sold by the H. C. Spinks Clay Company, Inc. of Highway 79 South, Paris, Tenn. This clay contains 60.9 percent of silica, 25.5 percent of alumina, and 1.6 percent of titania.

The nepheline syenite is charged via line 73 and the ball clay is charged via line 75. These ingredients are mixed in mixer 71 until a substantially homogeneous dry mixture is produced.

The dry binder mixture from mixer 71 is then discharged via line 77 to mixer 79. From about 10 to about 15 weight percent of this binder is charged to mixer 79.

Also charged to mixer 79, via line 81, is a preferred polyethyelne glycol or methoxypolyethylene glycol binder, such as, e.g., "Carbowax 20M". From about 0.5 to about 3.0 weight percent of such binder is preferably dissolved in water and the solution thereof is charged via line 81. Typically a 10 to 20 weight percent solution of the binder is used.

In one preferred embodiment, from about 82 to about 90 weight percent of fused alumina is charged to mixer 79 via line 83. One may use commercially available fused alumina such as, e.g., the 180 grit white fused alumina available from the Treibacher Schleifmettel Corporation of 2000 College Avenue, Niagara Falls, N.Y. 14302.

Referring again to FIG. 7, and in the preferred embodiment depicted therein, the binder solution is charged to mixer 79 via either line 81 and/or 83. The mixed slurry or paste may then be discharged via line 85 to dryer 87. Thereafter, the dried mixture may be discharged via line 89 to press 91.

Referring again to FIG. 7, the fired sheath body from furnace 69 is passed via line 95 to press 91. Referring to FIG. 3, the dried powder mixture from mixer 79 or dryer 87 is pressed and compacted within the channel 22 of sheath 14 with a punch.

The sheath with the powder mixture disposed within channel 22 is then passed via line 97 to furnace 99. Thereafter, this assembly is subjected to a temperature of from about 1,170 to about 1,200 degrees centigrade for at least about 1 hour until the powder disposed within channel 22 has been fired to form a rigid, porous body.

Figure 8:
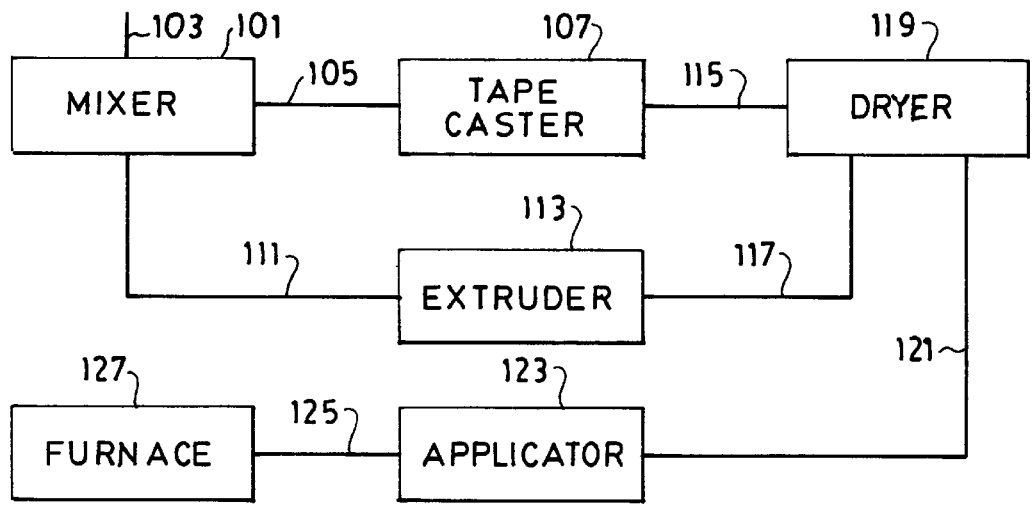
FIG. 8 is a flow diagram illustrating another preferred process of the invention.

FIG. 8 is a flow diagram of a preferred process for tape casting an assay of this invention. Referring to FIG. 8, to mixer 101 is charged (via line 103) calcined alumina, water, cellulose ether binders, and film-forming binder wax described elsewhere in this specification with reference to the mixture in mixer 53 (see FIG. 7). The mixture may be identical to the prior mixture or similar thereto. The mixture thus formed is then passed either via line 105 to tape caster 107, or via line 111 to an extruder 113. The green body thus formed is then passed via either line 115 or 117 through an air- or infrared- or microwave dryer 119 until it contains less than about 1 weight percent of moisture.

The dried green body is then passed via line 121 to applicator 123 in which a coating of porous ceramic is selectively applied to the base ceramic material. The composite material is then passed via line 125 to furnace 127, wherein it is heated until it reaches the desired density.

Figure 9:
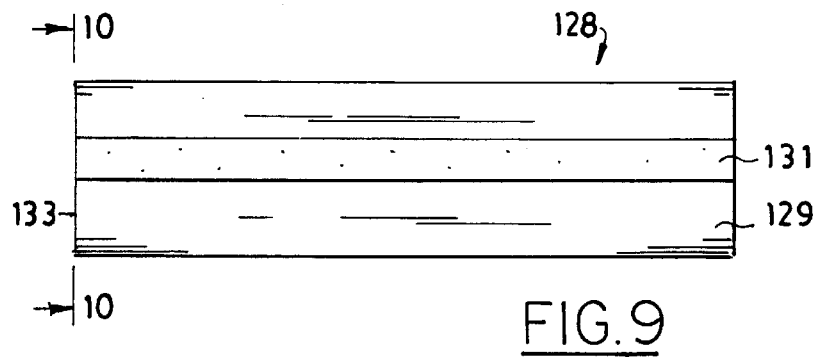
FIG. 9 is a top view of another assay assembly of the invention.
Figure 10:
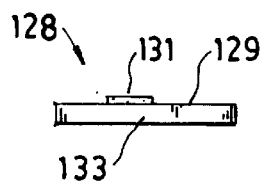
FIG. 10 is an end view of the assay assembly of FIG. 9.

FIG. 9 is a top view of one preferred assembly 128 produced in accordance with the process of FIG. 8, and FIG. 10 is an end view of such assembly. Referring to such figures, it will be seen that assembly 128 is comprised of a substantially non-porous base 129 to which is integrally connected a strip 131 of substantially porous ceramic material which has the properties described elsewhere in this specification for ceramic core 12. When bottom surface 133 is contacted with analyte, the analyte will preferentially diffuse up strip 131 in the manner described elsewhere in this specification and, with suitable visual indicator, will provide visual contrast between the surfaces of strip 131 through which the analyte has migrated and the surfaces of base 129 through which the analyte has not migrated. Suitable indicia (not shown) may be affixed to either base 129 and/or strip 131 to help indicate the extent of migration of analyte.

In one embodiment, the coefficients of thermal expansion of base material 129 and strip material 131 are within about 5 percent of each other.

Figure 11:
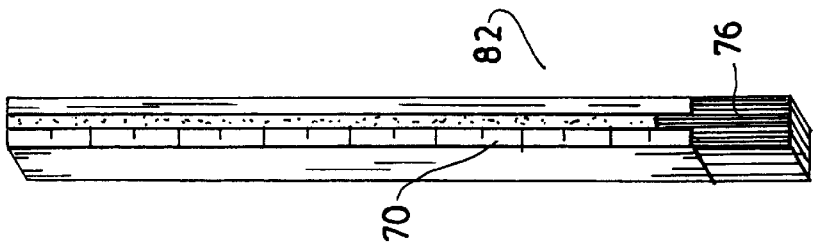
FIGS. 11, 12, and 13 are perspective views of the assay assembly of FIG. 1 in assays of low, medium, and high concentrations of the analyte being measured.
Figure 12:
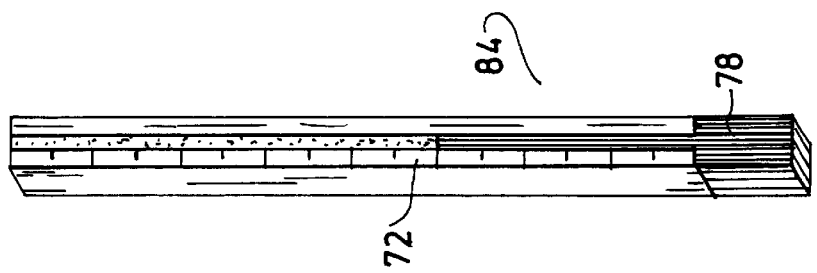
Figure 13:
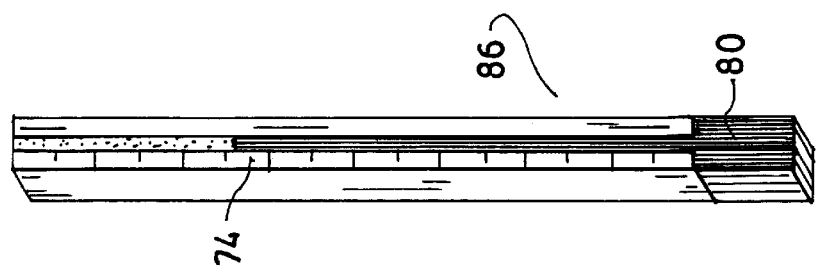

FIGS. 11, 12, and 13 illustrates the use of EIC/LAS in typical assays of low, medium, and high concentrations of the analyte being measured. The ceramic support is formed by casting, molding or extrusion of, e.g., a ceramic suspension, as described above. Functional groups are added to the ceramic support with the use of a material such as amino-propyl-triethoxysilane, which couples to the molecules in the ceramic (such as the silicon oxide particles) to yield available amino groups for further derivatization.

As described elsewhere in this specification, the reagent is coupled to the amino functional support by activation with glutaraldehyde, then by adding the reagent to the pores of the ceramic support to react with the activated functional groups.

In EIC, the immobilized reagent will typically be an antibody directed against the analyte to be measured, and a detectable reagent will be labeled analyte. As illustrated in FIGS. 11, 12, and 13, and in the embodiment depicted in these figures, the device consists of two regions: a glazed region 70, 72, and 74, which is graduated, and an unglazed region 76, 78, and 80, which is porous. The immobilized reagent is dispersed throughout the unglazed region.

When the device is then inserted into a sample containing a liquid mixture of labeled reagent and assay sample, the mixture diffuses through the porous ceramic, and the analyte and the labeled reagent react with the immobilized reagent.

The visually detectable groups on the labeled reagent make it possible to readily visually detect the leading edge boundary of the furthest region or zone from the start of diffusion where the leading edge of the labeled reagent has been bound.

As is illustrated in FIGS. 11, 12, and 13, with greater amounts of free analyte, the leading edge of the labeled reagent is bound further from the start of diffusion; the greater displacement distance with higher free analyte concentrations is proportional to the concentration of free analyte. Thus, referring again to FIG. 11, situation 82 illustrates the result obtained with a low concentration of analyte, situation 84 illustrates the result obtained with a medium concentration of analyte, and situation 86 illustrates the result obtained with a high concentration of analyte.

As will be apparent to those skilled in the art, the assay of this invention can be used for screening purposes (to indicate the presence of absence of a detectable level of analyte, by a positive or negative visual result). Alternatively, or additionally, it may be used to quantitatively determine the amount of analyte present, such amount being proportional to its migration of its leading edge of detectable reagent up the porous ceramic structure.

Figure 14:
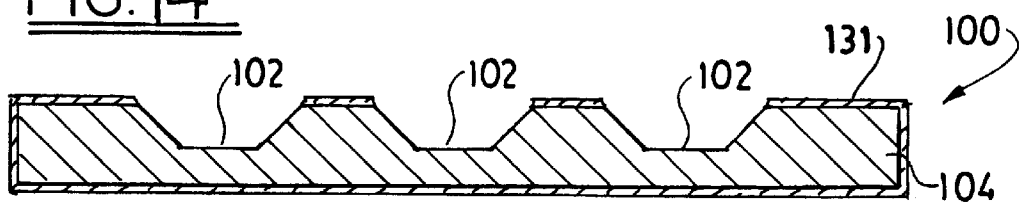
FIG. 14 is a sectional view of a dot-type screening device.
Figure 15:
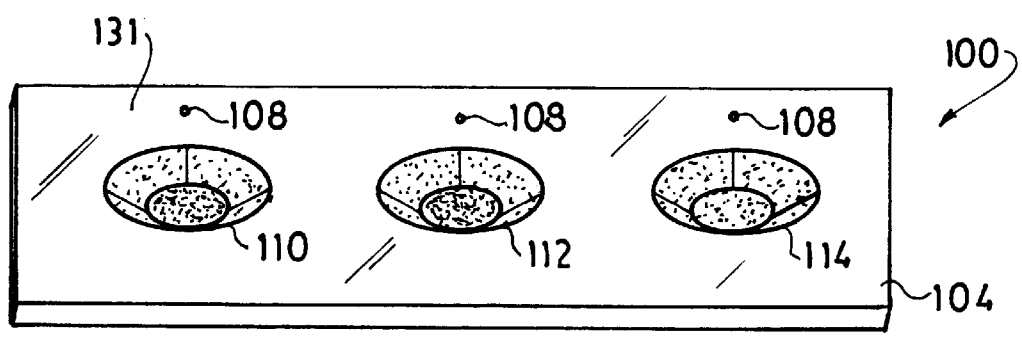
FIG. 15 is a perspective view of a dot-type screening device of FIG. 14.
Figure 16:
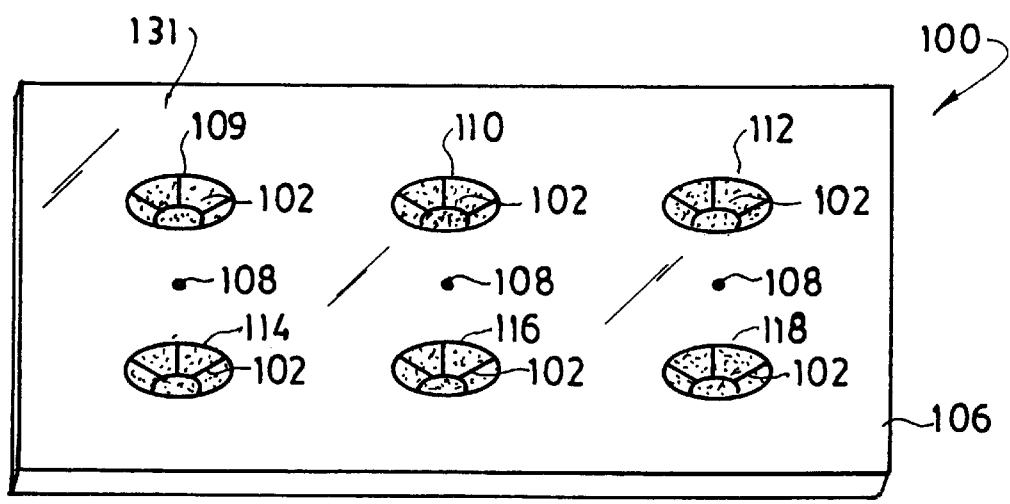
FIG. 16 is a perspective view of another dot-type screening device.

FIGS. 14, 15, and 16 illustrate the construction of one preferred embodiment a ceramic device for use in dot-type screening assays. FIG. 14 is a sectional view of the device of FIG. 15.

As is illustrated in FIGS. 14, 15, and 16, assay device 100 contains wells 102 which are formed as depressions of porous ceramic within a glazed slab 104 or 106. Vents 108 provide an escape for air within the porous ceramic when liquid sample is placed in the wells. The glaze 130 is preferably applied in all areas except the wells 102 or similar depressions.

As is illustrated in FIG. 15, one well 110 serves as the test well, where, in the case of the colored particle labeled reagent, a positive test is indicated by the appearance of color in the well. Wells 112 and 114 serve as positive and negative controls, respectively.

As is illustrated in FIG. 16, multiple samples or analytes can be assayed using a single ceramic slab 106. The control sample is applied to well 109. Separate samples can be applied to wells 110, 112, 114, 116, and 118. The detectable reagent, added to these wells after the sample, can be the same as the immobilized reagent in each well. Alternatively, the detectable reagent can be different from the immobilized reagent in each well, thereby creating different immobilized and detectable reagent combinations. Such combinations provide a device for detection of multiple analytes within the same sample.

The devices illustrated in FIGS. 14, 15, and 16 may be formed in the same way as the devices shown in FIGS. 1–5, with the exceptions that uncoupled reagent need not be removed until the sample is added, and unreacted analyte is removed by washing (which will also remove the uncoupled reagent). The assay using these devices is typically performed by adding sample to each well, allowing the sample to diffuse and analyte to react with immobilized and detectable reagent, then washing unbound sample material into surrounding pore areas. If the indicator is a colored particle, the test is read immediately. If the indicator is an enzyme, enzyme substrate and incubation are required before reading. In a sandwich dot assay, a positive is indicated by the presence of color at the bottom of the well. In a competitive binding dot assay, a positive is indicated by the absence of color in the bottom of the well.

Other shapes, numbers of test sites, and configurations will be readily apparent to those skilled in the art. For example, devices can also be formed by the machining of a slab of material. In one embodiment, not shown, a device is extruded as a slab and then fired, and depressions of the appropriate dimensions are then machined into the surface of the slab.

Figure 17:
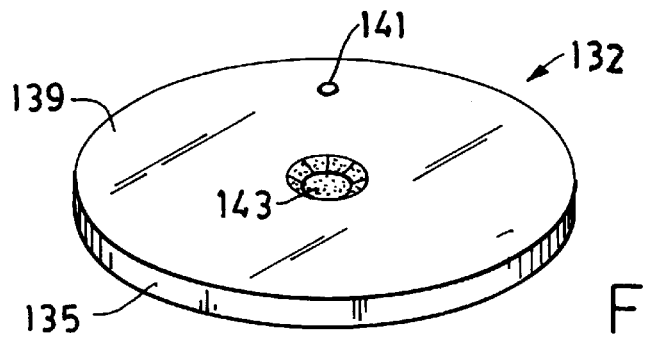
FIG. 17 is a perspective view of another assay assembly of the invention.

FIG. 17 is a perspective view of yet another preferred assay device 132 which preferably is comprised of at least about 95 weight percent of porous, hydrophilic ceramic material 135 which, preferably, has properties similar to that possessed by the ceramic material with core 12. The assay device 132 is preferably selectively coated with an impermeable coating material (such as glaze or wax) which preferably only allows the passage of liquid or gas thorough either vent hole 141 and/or well 143. The vent hole 141 allows air to escape from the porous ceramic material as reagent enters the reaction zone 143. The reaction zone/well 143 is the site in which free analyte and/or analyte attached to a detectable group is trapped by immobilized ligand.

As will be apparent to those skilled in the art, other devices may be used with other shapes, and/or differing number of vent holes, and/or differing numbers of wells.

It is preferred that the assembly 132, when immersed in distilled water for 1 minute, absorb at least about 0.25 cubic centimeters of water. The amount so absorbed can be readily determined by weighing assembly 132 prior to and after immersion.

Figure 18:
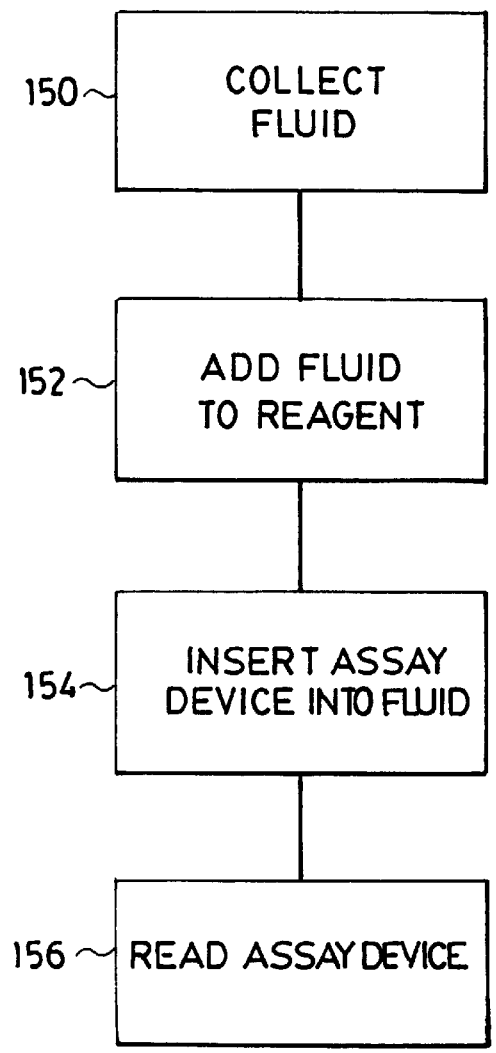
FIG. 18 is a flow diagram illustrating one preferred process for using a particular assay assembly of the invention.

FIG. 18 is a flow diagram of a preferred process of using the assay device of this invention.

In step 150 of the process depicted in FIG. 18, the fluid to be tested is collected. Thus, e.g., a patient's finger could be pricked to obtain blood for testing.

In step 152 of the process depicted in FIG. 18, the collected fluid is added to reagent. Thus, e.g., one could add a capillary with blood to a vial of analytical reagent and thereafter mix well.

In step 154 of the process, an assay assembly (such as assembly 10 of FIG. 1) is inserted into the fluid/reagent mixture. Thus, e.g., the device 10 of FIG. 1 may be insert ed into the blood/analytical reagent mixture. The mixture is allowed to migrate up the device until the liquid level reaches the top.

In step 156 of the process, the assay device is read. Thus, e.g., the device 10 can be removed from the blood/analytical reagent vial. Thereafter, the height of the colored column can be read against the gradation scale to obtain the results. The total time required to perform this assay is estimated to be about ten minutes.

Figure 19:
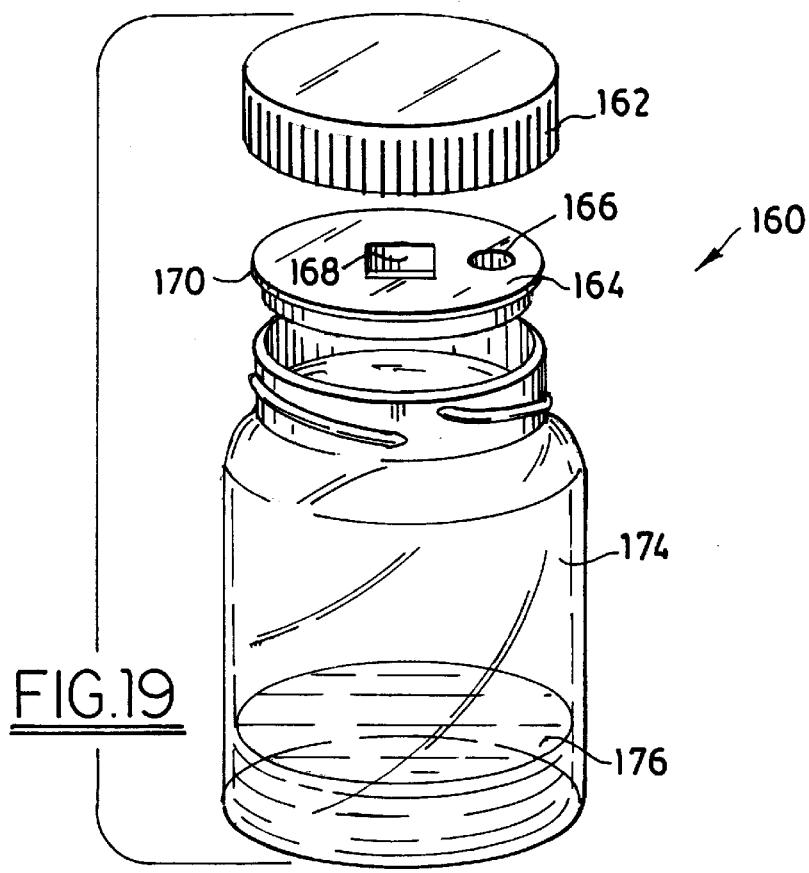
FIG. 19 is an exploded view of a container which may be used in conjunction with the assay assembly of FIG. 1.
Figure 20:
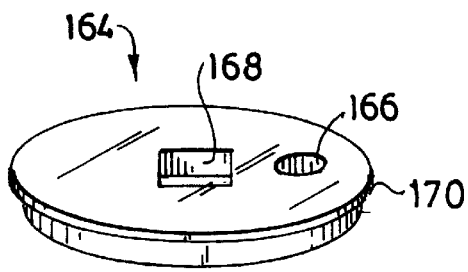
FIG. 20 is a perspective view of a lid portion of the container of FIG. 19.
Figure 21:
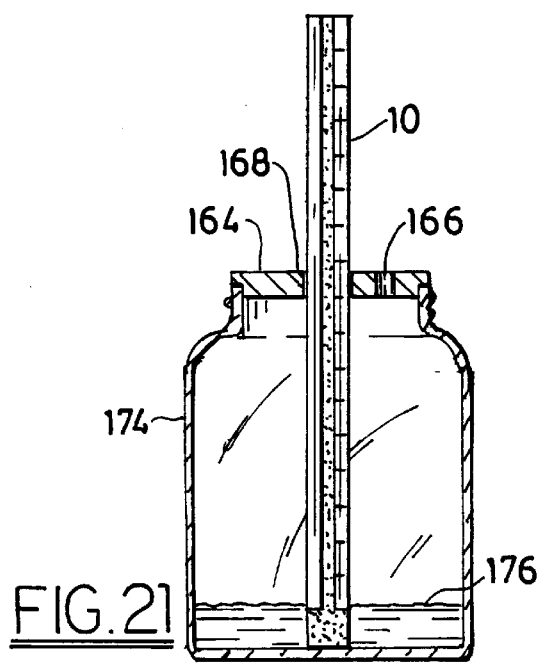
FIG. 21 is a sectional view illustrating the assay assembly of FIG. 1 disposed within the container of FIG. 19.

FIG. 19 is an exploded view of an assay assembly 160 which is comprised of a vial 174 in which analytical reagent 176 is disposed. A removable lid 170 may be disposed (friction fit) within the mouth of vial 174. The removable lid 170 is comprised of hole 166 (through which liquid to be tested may be inserted) and orifice 168 (through which the assay assembly 10 may be inserted).

Removable cap 162 is adapted to engage threads on the neck of vial 174. Thus, vial 174 may be shipped with reagent 176 in place without risk of losing such reagent.

In order to perform an assay, one may remove cap 162, add the reagent to be tested through orifice 166, and then insert assay assembly 10 through orifice 168 until it is contiguous with the interior bottom wall of vial 174. Thereafter, in accordance with the process described in FIG. 18, the assay assembly 10 is removed and read.

FIG. 22 illustrates a linear assay device 200 in which a specified amount of antigen-containing sample is placed prior to testing for the presence of antigen.

Referring to FIG. 22, it will be seen that assay assembly 200 is comprised of a well 202 in which a specified amount of antigen-containing sample (such as blood from animal) is placed. Because well 202 has a specified volume, it will only accept a specified, known volume of such sample. In one embodiment, for example, the volume of well 202 is from about 75 to about 80 cubic millimeters.

In the preferred embodiment depicted in FIG. 22, assembly 200 has a length 204 of from about 70 to about 90 millimeters and, preferably, from about 75 to about 85 millimeters. In one aspect of this embodiment, length 204 is about 80 millimeters.

Referring again to FIG. 22, and in the preferred embodiment depicted therein, it will be seen that assembly 200 preferably has a width of from about 8 to about 12 millimeters and, more preferably, from about 9 to about 11 millimeters. In this embodiment, the width 208 of ceramic core 12 is preferably from about 1.8 to about 2.2 millimeters and end 210 of assembly 200.

FIG. 23 is a side view of the assembly 200 of FIG. 22. Referring to FIG. 23, it will be seen that, in the preferred embodiment depicted, assembly 200 preferably has a height 212 of from about 4 to about 6 millimeters and, preferably, from about 4.5 to about 5.5 millimeters. In one preferred embodiment, height 212 is about 5.0 millimeters.

Referring again to FIG. 23, it will be seen that ceramic core 12 is disposed within sheath 14 at a depth 214 which is preferably from about 1 to about 2 millimeters. In one preferred embodiment, depth 214 is about 1.5 millimeters.

FIG. 24 is an end view of assembly 200.

In one preferred embodiment, the assembly 200 of FIGS. 22–24 is used in conjunction with an assay process for determining whether a domestic animal is pregnant. This process is illustrated in the flow diagram of FIG. 25.

Figure 25:
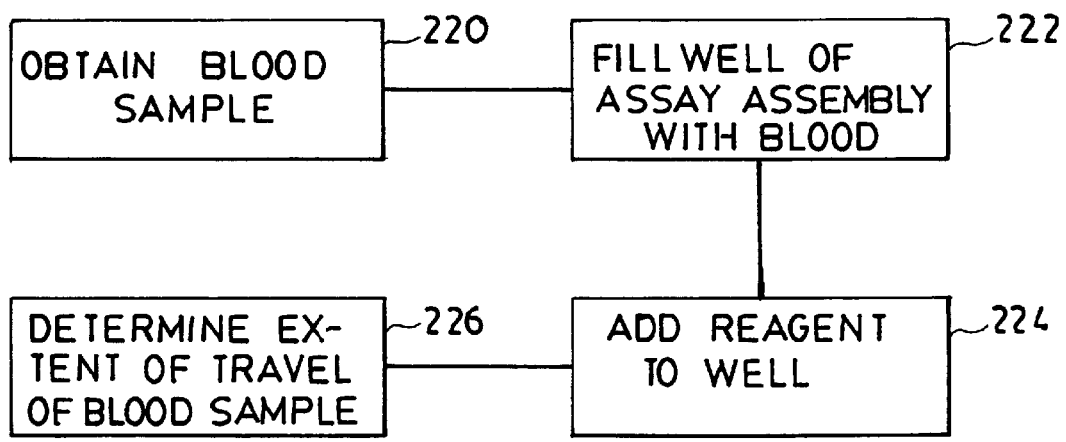
FIG. 25 is flow diagram illustrating one preferred process of the invention.

In the first step of the process depicted in FIG. 25, step 220, blood is drawn from the domestic animal by conventional means such as, e.g., with the use of a lancet. Thus, e.g., one may use a lancet such as that the "MINILANCE" lancet depicted as product B-D number 5757 on page 544 of the 1993/1994 Fisher Catalog. Alternatively, one may use the "MICROTAINER" capillary blood collection device depicted on page 545 of such catalog.

Referring again to FIG. 25, and in step 222 thereof, the blood sample collected is deposited in well 202 (see FIG. 22) until such well is filled with the blood.

Thereafter, in step 224, from about one to about two drops of a reagent containing latex beads is added to the well. These beads diffuse up the assembly 200 together with the blood sample. The extent of diffusion, and travel, is dependent upon the concentration of antigen present in the blood sample.

Alternatively, or additionally, one may use other labels for the analyte or the antibody reagents to facilitate measurement. The reagent which is immobilized to the porous support generally is not labeled, although it can be in certain ceases where reaction with the indicator of pregnancy elicits a directly detectable event. In most cases, a second reagent which is freely diffusible within the porous support is labeled and binding of immobilized reagent with analyte is indirectly detected.

In one preferred embodiment, homogeneous dispersed within the porous ceramic material 12 is an antibody (or a reactive fragment thereof) for one or more of antigens selected from the group consisting of relaxin, estrogens, progesterone, early pregnancy factor, placental lactogen, gonadotrphins, and pregnancy associated antigens and combinations thereof. It is preferred that the antibody be an antibody for an antigen selected from the group consisting of estrone sulfate, estrone glucuronide, estradiol sulfate, estradiol glucuronide, and progesterone. The antibodies for these antigens are well known to those skilled in the art. Thus, e.g., reference may be had to applicants' provisional patent application 60/007,509, filed on Nov. 22, 1995, the entire disclosure of which is hereby incorporated by reference into this specification.

Thus, for example, the antibodies for estrone gluocuroide and estradiol gluocuronide are described in an article by S. W. Chen et al. entitled "Determination of pregnancy and estimation of litter size in gilts . . . " which appeared in Animal Reproduction Science 39 (1995).

Thus, for example, the antibody for estrone sulfate is described in an article by D. F. M. van de Wiel et al. entitled "Pregnancy diagnosis in sows . . . " which was published in Livestock Production Science, 32 (1992), at pages 323–330.

Thus, for example, a survey of various "Pregnancy Diagnosis" tests is presented at pages 293-304 of a book edited by D. J. Cole et al. entitled "Control of Pig Reproduction" (Butterworth, United Kingdom, 1982).

Thus, by way of further illustration, the use of various antibodies in pregnancy testing is disclosed in one or more of U.S. Pat. Nos. 4,016,250, 4,744,368, 4,869,260, 4,094, 963, 4,268,435, 4,256,629, 4,508,829, 5,108,897, 5,169,835, and the like. The entire disclosure of each of these United States patents is hereby incorporated by reference into this specification.

Referring again to FIG. 25, after a specified period of time (usually about six minutes), in step 226 the extent of the travel of the blood sample is determined by visually inspecting the assay device 200. As will be apparent to those skilled in the art, the greater the presence of the antigen in the blood sample, the further the blood sample (and the associated latex bead reagent) will travel.

Although the process has been described with respect to a blood sample, or bodily materials of the domestic animal which also contain the pregnancy antigen may be used. Thus, e.g., may use a sample of the animals urine, or of its feces.

The following examples are presented to illustrate the claimed invention and is not to be deemed limitative thereof.

Unless otherwise specified, all parts are by weight, and all temperatures are in degrees Centigrade.

EXAMPLE 1

"Major slip", a casting slip comprised of ball clay and talc, was purchased from the Bercher Ceramic Supplies Corporation of Oklahoma City, Okla.

In substantial accordance with the procedure described in the specification, a negative plaster mold was prepared with strip cavities to produce the shape depicted in FIG. 1 with mold dimensions of 6 millimeters×6 millimeters×110 millimeters. The strip cavities in the mold were filled with the casting slip, which was allowed to stay within the strip cavities while the water within it diffused through the mold walls for 60 minutes. Thereafter, the green bodies thus formed were removed from the strip cavities, placed on a support, and allowed to air dry for 24 hours.

A wax-glaze resist material ("Wax-Resist", sold by the Duncan Corporation of Fresno, Calif.) was applied to the dried supports to separate them into porous and sealed regions. Referring to FIG. 1, the resist material was applied to those areas which are indicated to be comprised of porous, hydrophilic material (see element 12).

A clear glaze ("Infinity Gaze—Clear", sold as catalog number IN1001 by the Duncan Corporation) was applied to all of the non-protected areas of dried supports (front, back, and sides) and allowed to dry under ambient conditions for 20 minutes.

The dried supports were then placed into a model DA 820 furnace (sold by Bercher Ceramic Supplies). The temperature of the furnace was then raised to cone 6, the supports were than allowed to soak at this temperature about 12 hours, and the supports were then cooled to ambient. The firing was performed in air.

EXAMPLE 2

Competitive assays using radiolabelled antigen and antibody to estrone sulfate were performed to determine estrone sulfate levels in serum samples. Since these were competitive assays, a rise in estrone sulfate level is indicated by a decrease in radioactivity measurement.

In the first set of reactions, 100 microliters of estrone $I^{125}$ was added to each 50 microliters of each sample as indicated, except for the control, a non-reactive nucleotide storage buffer (NSB) being 150 microliters. One hundred microliters of monoclonal antibody to estrone sulfate, obtained from AgResearch, New Zealand, was added to each sample, except the NSB, incubated for one hour and then vortexed. One thousand microliters of precipitating reagents were then added for a 15 minute incubation. The results are shown below in Table 1, wherein standards 1 to 3 are estrone sulfate standards. The samples indicated by "Day" refer to serum obtained from pigs at the indicated day of breeding.

TABLE 1

| SAMPLE | CPM |
| --- | --- |
| 1) Total Count | 26,2702 |
| 2) Level II | 4,695.81 |
| 3) NSB (0 pg/ml) | 5,330.0 |
| 4) Stand A (0 pg/ml) | 10,864.21 |
| 5) Stand D (100 pg/ml) | 7,138.25 |
| 6) Stand D (100 pg/ml) | 7,088.97 |
| 7) Stand E (300 pg/ml) | 5,007.00 |
| 8) Stand F (900 pg/ml) | 3,578.93 |

TABLE 1-continued

| SAMPLE | CPM |
| --- | --- |
| 9) Stand 1 (100 pg/ml) | 11,152.22 |
| 10) Stand 2 (100 pg/ml) | 10,909,19 |
| 11) Stand 3 (1,000 pg/ml) | 10,427.69 |
| 12 Day 0 | 11,408.89 |
| 13) Day 19 | 10,903.16 |
| 14) Day 25 | 10,540.00 |

In a second set of reactions, sulfatase enzyme was added. More specifically, 50 microliters of sample as indicated was combined with 10 microliters of sulfatase enzyme and incubated for 2 hours in a 37 degrees Centigrade bath. Ten microliters of estrone $I^{125}$ and 100 microliters of monoclonal antibody to estrone sulfate obtained from AgResearch, New Zealand were added and incubated for 1 hour. One thousand microliters of precipitating reagents were added for a 15 minute incubation. The results are shown below in Table 2. The * indicates that antibody was added.

TABLE 2

| SAMPLE | CPM |
| --- | --- |
| 1) Total Count | 23,864.44 |
| 2) Level II | 3,192.38 |
| 3) NSB* | 5,577.78 |
| 4) Stand A (0 pg/ml) | 7,227.86 |
| 5) Stand D (100 pg/ml) | 4,292.77 |
| 6) Stand D (100 pg/ml) | 3,783.77 |
| 7) Stand E (300 pg/ml) | 3,509.82 |
| 8) Stand F (900 pg/ml) | 2,330.70 |
| 9) Stand 1 (100 pg/ml) | 5,649,44 |
| 10) Stand 2 (500 pg/ml) | 5,291.05 |
| 11) Stand 3 (1000 pg/ml) | 4,173.75 |
| 12) Pig No. 2 Day 0 | 7,170.00 |
| 13) Pig No. 11 Day 19 | 6,670.67 |
| 14) Pig No. 15 Day 25 | 7,557.78 |

A third set of reactions was performed similar to the one above including sulfatase. Fifty microliters of sample was measured, except for 150 NSB, were combined with 10 microliters of estrone sulfatase for 3 hours in a 37 degree Centigrade bath. One hundred microliters of estrone $I^{125}$ and 100 microliters of monoclonal antibody to estrone sulfate obtained from AgResearch, New Zealand wee added (except to NSB) and incubated for 1 hour. One thousand microliters of precipitating agents were then added. The results are shown below in Table 3.

TABLE 3

| SAMPLE | 5 MIN. | 1 MIN. | CPM |
| --- | --- | --- | --- |
| 1) Total Count | 26,558.1 | 26,406.1 | 24,633.33 |
| 2) Level II | 3,995.9 | 4,055.4 | 2,473.83 |
| 3) NSB (0 pg/ml) | 627.5 | 615.2 | 583.2 |
| 4) Stand A (0 pg/ml) | 6,640.9 | 6,604.9 | 3,636.79 |
| 5) Stand D (100 pg/ml) | 4,083.0 | 4,110.6 | 2,498.02 |
| 6) Stand E (300 pg/ml) | 3,549.5 | 3,577.6 | 2,407.86 |
| 7) Stand F (900 pg/ml) | 2,552.0 | 2,589.3 | 1,803.0 |
| 8) Stand G (2000 pg/ml) | 1,987 | 1,983.2 | 1,587.4 |
| 9) Stand 1 (100 pg/ml) | 7,620.1 | 7,733.2 | 4,595.0 |
| 10) Stand 2 (500 pg/ml) | 5,827.3 | 5,766.3 | 3,830.19 |
| 11) Stand 3 (1000 pg/ml) | 4,878.5 | 4,851.5 | 3,361.0 |
| 12) Day 0 | 8,319.7 | 8,444.1 | 4,932.68 |
| 13) Day 0 | 8,456.9 | 8,402.7 | 5,425.41 |
| 14) Day 19 | 7,694.3 | 7,805.9 | 4,726.98 |
| 15) Day 19 | 6,734.9 | 6,705.3 | 4,200.42 |

TABLE 3-continued

| SAMPLE | 5 MIN. | 1 MIN. | CPM |
|---|---|---|---|
| 16) Day 25 | 8,498.2 | 8,529.6 | 5,377.37 |
| 17) Day 26 | 4,186.5 | 4,143.7 | 2,892.0 |

The following Table 4 demonstrates that estrone sulfate levels correlate with whether or not the pigs were actually present. Specifically, an y pigs which had an assay result of 6,862 cpm were predicted as being pregnant. Pregnancy was determined by whether birth resulted. The tests showed 100 percent accuracy. Fifty microliters of each sample as indicated was used except that 150 microliters of NSB was used. en microliters of estrone sulfatase was added and incubated for 4 hours. One hundred microliters of estrone $I^{125}$ and 100 microliters of estrone sulfate monoclonal antibody were added to each sample except the NSB sample, incubated for 1 hour and then vortexed. One thousand microliters of precipitating agents were then added. The total count measured was 100 microliters of esterone $I^{125}$. The "P" under the pregnancy column indicates that the pig was in fact pregnant.

| SAMPLE | CPM | PREGNANT | NOT PREGNANT |
|---|---|---|---|
| 1) Total Count | 22,400 | | |
| 2) NSB | 744 | | |
| 3) Level II | 3,422 | | |
| 4) Stand A (0 pg/ml) | 8270 | | |
| 5) Stand B (15 pg/ml) | 6,645 | | |
| 6) Stand D (100 pg/ml) | 3,774 | | |
| 7) Stand E (300 pg/ml) | 3,303 | | |
| 8) Stand F (900 pg/ml) | Faulty/Inadequate | | |
| 9) Stand G (2000 pg) | 1,960 | | |
| 10) Stand 1 (100 pg) | 6,862 | | |
| 11) Stand 2 (500 pg) | 5,226 | | |
| 12) Stand 3 (1000 pg) | Bad | | |
| 13) Day 0 | 7,489 | | NOT |
| 14) Day 0 | 8,178 | | NOT |
| 15) Day 0 | 7,813 | | NOT |
| 16) Day 0 | 8,240 | | NOT |
| 17) Day 0 | 7,560 | | NOT |
| 18) Day 15 | 7,984 | | NOT |
| 19) Day 17 | 7,821 | | NOT |
| 20) Day 18 | 6,654 | P | |
| 21) Day 19 | 4,632 | P | |
| 22) Day 19 | 7,210 | | NOT |
| 23) Day 19 | 7,151 | | NOT |
| 24) Day 19 | 6,311 | P | |
| 25) Day 19 | 5,632 | P | |
| 26) Day 25 | 7,816 | | NOT |
| 27) Day 25 | 7,995 | | NOT |
| 28) Day 25 | 3,716 | P | |
| 29) Day 26 | 3,723 | P | |
| 30) Day 26 | 2,645 | P | |
| 31) Day 26 | 3,137 | P | |
| 32) Day 35 | 7,712 | | NOT |
| 33) Day 35 | 6,507 | P | |
| 34) Day 35 | 6,698 | P | |
| 35) Day 34 | 7,860 | | NOT |

The samples from ten sows which had assay results showing under 6,862 cpm were predictive of these sows being pregnant. The samples of the sows which were predicted to be and in fact were pregnant had an average cpm of 4,938.5. All of these sows gave birth at 114 to 118 days after insemination. Thirteen sows had samples with assay results over 6,836 cpm and were determined to be not pregnant as they did not give birth at the end of the gestation period. The results of the assays showed that samples from the non pregnant sows had an average cpm of 7,703.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

Thus, by way of illustration, instead of or in addition to the aforementioned porous ceramic material within ceramic core 12, one may use other porous materials such as nylon, paper, porous plastics (such as nitrocellulose), naturally occurring rock, and the like.

Thus in one embodiment, not shown, the ceramic core 12 is used as a self-supporting entity without sheath 14.

Thus, in an embodiment comparable to that depicted in FIG. 10, the ceramic strip 131 is contiguous with non-ceramic slab for only from about 20 to about 40 percent of its perimeter.

We claim:

1. An assembly for use in biological assays, wherein said assembly is comprised of an integral ceramic core with a top surface and a bottom surface, and, contiguous with and integrally connected to a portion of said ceramic core, a sheath with a top surface and a bottom surface, and wherein:

(a) said ceramic core has a mean pore size of from about 1 to about 400 microns and an apparent porosity of from about 25 to about 60 percent, (b) said ceramic core has a hydrophilic surface, wherein at least a portion of said hydrophilic surface is not contiguous with said sheath, (c) said ceramic core has a length of from about 10 to about 200 millimeters, (d) said ceramic core has a thickness which is at least about ten times as great as said mean pore size of said ceramic core, (e) when said bottom surface of said ceramic core is placed in distilled water at a temperature of 25 degrees centigrade, said distilled water is wicked towards said top surface of said ceramic core at a first wicking rate of at least 20 millimeters per minute, (f) when said bottom surface of said sheath is placed in distilled water at a temperature of 25 degrees centigrade, said distilled water is wicked towards said top surface of said sheath at a second wicking rate of less than 5 millimeters per minute, (g) the ratio of said first wicking rate to said second wicking rate is at least about 4, (h) said ceramic core has a cross-sectional perimeter of from about 2 to about 32 millimeters, (i) from about 20 to about 90 percent of said perimeter of said ceramic core is contiguous with said sheath, and (j) substantially homogeneously disposed throughout said ceramic core is from about 0.01 to about 1.0 weight percent of a biologically active molecule.

2. The assembly as recited in claim 1, wherein said biologically active molecule is selected from the group consisting of proteins, polysaccharides, lipids, lipoproteins, and nucleic acid sequences.

3. The assembly as recited in claim 2, wherein said biologically active molecule is an antibody.

4. The assembly as recited in claim 3, wherein said antibody is immunoreactive with an antigen selected from the group consisting of estrone sulfate, estrone glucuronide, estradiol sulfate, and estradiol glucuronide, and progesterone.

5. The assembly as recited in claim 4, wherein said sheath is in the form of a slab of ceramic material.

6. The assembly as recited in claim 5, wherein said ceramic core is in the form of a strip of ceramic material partially contiguous with said slab of ceramic material.

7. The assembly as recited in claim 4, wherein said ceramic core is disposed in a channel disposed within said sheath.

8. The assembly as recited in claim 7, wherein said channel has a depth of from about 1 to about 5 millimeters.

9. The assembly as recited in claim 4, wherein said ceramic core has a mean pore size of from about 5 to about 20 microns and an apparent porosity of from about 35 to about 55 percent.

10. The assembly as recited in claim 4, wherein said ceramic core has a surface which is substantially opaque.

* * * * *